United States Patent [19]

Dinsmore et al.

[11] Patent Number: 5,442,678

[45] Date of Patent: Aug. 15, 1995

[54] X-RAY SOURCE WITH IMPROVED BEAM STEERING

[75] Inventors: Mark T. Dinsmore, Sudbury; Donald O. Smith, Lexington, both of Mass.

[73] Assignee: Photoelectron Corporation, Waltham, Mass.

[21] Appl. No.: 184,021

[22] Filed: Jan. 21, 1994

Related U.S. Application Data

[63] Continuation-in-part of Ser. No. 955,494, Oct. 2, 1992, Pat. No. 5,369,679, which is a continuation-in-part of Ser. No. 577,883, Sep. 5, 1990, Pat. No. 5,153,900.

[51] Int. Cl.⁶ .............................................. A61N 5/10
[52] U.S. Cl. .................................. 378/137; 378/119; 378/138; 378/121
[58] Field of Search ............... 378/119, 121, 137, 138, 378/143, 145, 113, 64, 65

[56] References Cited

U.S. PATENT DOCUMENTS

| | | | |
|---|---|---|---|
| 1,981,583 | 11/1934 | Craig . | |
| 2,362,816 | 11/1944 | Harker | 378/138 |
| 2,531,583 | 11/1950 | Ott | 378/137 |
| 2,748,294 | 5/1956 | Reinger . | |
| 2,946,892 | 7/1960 | Bas-Taymaz | 378/137 |
| 3,609,432 | 9/1971 | Shimura | 378/143 |
| 3,668,454 | 6/1972 | Shimura | 378/137 |
| 3,714,486 | 1/1973 | McCrary | 378/122 |
| 3,752,990 | 8/1973 | Fischer | 378/38 |
| 3,920,999 | 11/1975 | Drexler et al. | 378/119 |
| 4,104,531 | 8/1978 | Weiss | 378/38 |
| 4,104,532 | 8/1978 | Weiss | 378/38 |
| 4,109,154 | 8/1978 | Taumann | 378/159 |
| 4,117,334 | 9/1978 | Strauts | 378/102 |
| 4,157,475 | 6/1979 | Stock et al. | 378/147 |
| 4,205,251 | 5/1980 | Zwep | 378/121 |
| 4,344,181 | 8/1982 | Baecklund | 378/45 |
| 4,517,472 | 5/1985 | Ruitberg et al. | 378/102 |
| 4,563,769 | 1/1986 | Madsen | 378/121 |
| 4,608,977 | 9/1986 | Brown | 606/130 |
| 4,646,338 | 2/1987 | Skillicorn | 378/110 |
| 4,694,480 | 9/1987 | Skillicorn | 378/119 |
| 4,789,997 | 12/1988 | Madsen et al. | 378/109 |
| 4,856,036 | 8/1989 | Malcolm et al. | 378/116 |
| 4,924,485 | 5/1990 | Hoeberling | 378/102 |
| 5,090,043 | 2/1992 | Parker et al. | 378/121 |
| 5,116,344 | 5/1992 | Sundquist | 606/130 |
| 5,116,345 | 5/1992 | Jewell et al. | 606/130 |
| 5,165,093 | 11/1992 | Miller et al. | 378/138 |

Primary Examiner—David P. Porta
Assistant Examiner—Don Wong
Attorney, Agent, or Firm—Lappin & Kusmer

[57] ABSTRACT

This invention is directed to an x-ray source comprising a housing, an elongated tubular probe, a target assembly, and a beam steering assembly. The housing encloses an electron beam source, and has elements for generating an electron beam along a beam path. The elongated tubular probe extends along a central axis from the housing about the beam path. The target assembly extends along the central axis and is adapted for coupling to the end of the probe distal form the housing. The target assembly includes a target element positioned along the beam path, wherein the target element is adapted to emit x-rays in a predetermined spectral range in response to incident electrons. The beam steering assembly includes a deflection element, a feedback network, and a deflection controller. The deflection element deflects the beam from a nominal axis to a selected surface region on the target element in response to a deflection control signal. The feedback network includes deflection sensing elements for sensing the deflection of the beam and elements for generating a feedback signal representative thereof. The deflection controller couples to the deflection element and to the feedback network and includes elements for generating a deflection control signal in response to the feedback signal.

18 Claims, 15 Drawing Sheets

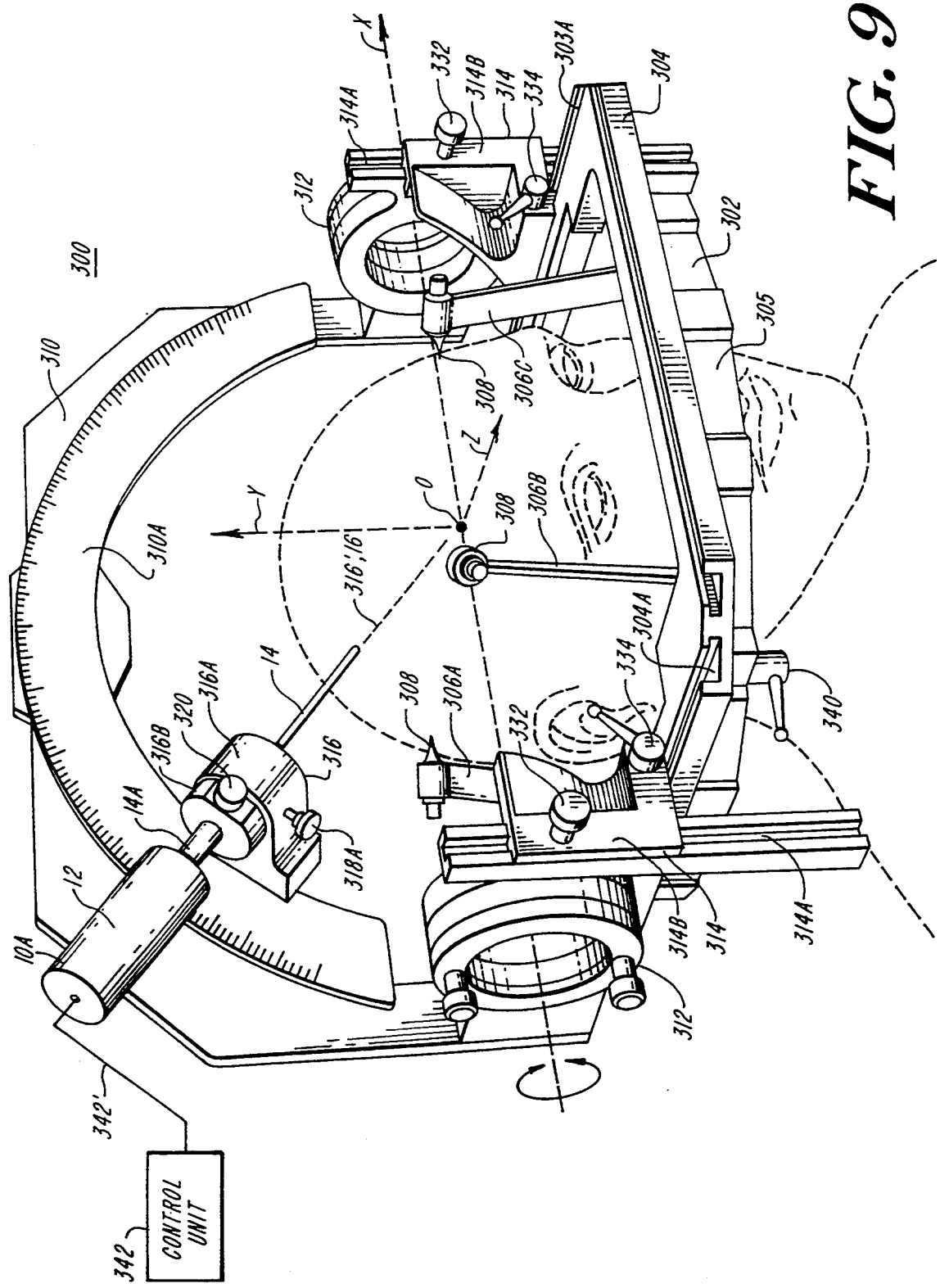

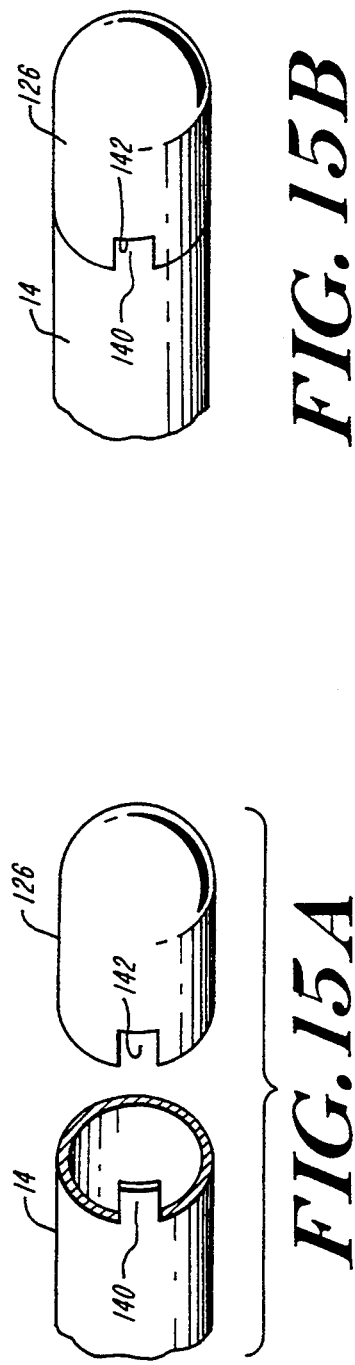
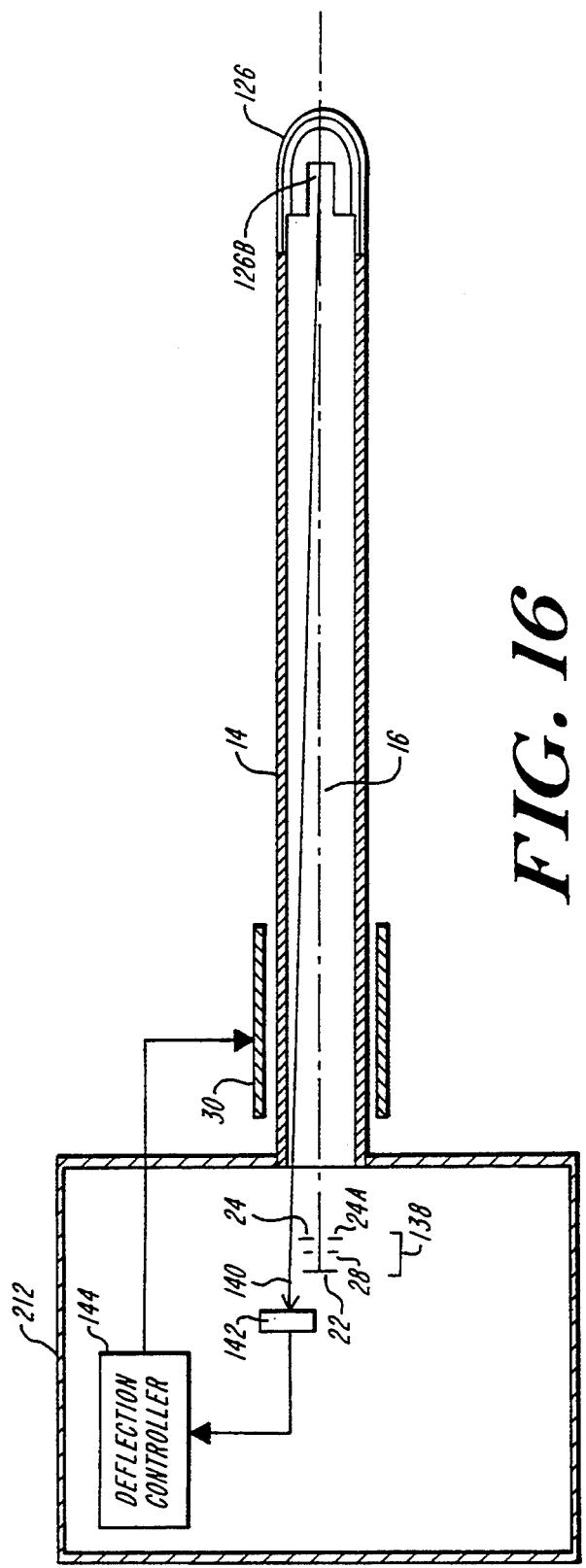

X-RAY SOURCE WITH IMPROVED BEAM STEERING

REFERENCE TO RELATED APPLICATION

This application is a continuation-in-part of U.S. patent application Ser. No. 955,494, entitled LOW POWER X-RAY SOURCE WITH IMPLANTABLE PROBE FOR TREATMENT OF BRAIN TUMORS, filed Oct. 2, 1992, now U.S. Pat. No. 5,369,679 assigned to the assignee of the present application, which is a continuation-in-part of U.S. patent application Ser. No. 577,883, now U.S. Pat. No. 5,153,900, entitled MINIATURIZED LOW POWER X-RAY SOURCE, filed Sep. 5, 1990, assigned to the assignee of the present application. The subject matter of this application is related to that of U.S. patent application Ser. No. 08/184,271 entitled X-RAY SOURCE WITH SHAPED RADIATION PATTERN, and U.S. patent application Ser. No. 08/184,296 entitled X-RAY SOURCE WITH FLEXIBLE PROBE, filed on even date herewith.

BACKGROUND OF DISCLOSURE

The present invention relates to a miniaturized, low power, programmable x-ray source for use in delivering low-levels of substantially constant or intermittent x-rays to a specified region.

Conventional medical x-ray sources are large, fixed position machines. Generally, the head of the x-ray tube is placed in one room and the control console in an adjoining area, with a protective wall, equipped with a viewing window, separating the two. The x-ray tube typically is approximately 20 to 35 centimeters (cm) long, and approximately 15 cm in diameter. A high voltage power supply is housed within a container located in a corner of the room containing the x-ray tube. Patients are brought to the machine for diagnostic, therapeutic, or palliative treatment.

Diagnostic x-ray machines are typically operated at voltages below 150 kilovolts (kV), and at currents from approximately 25 to 1200 milliamps (mA). By contrast, the currents in therapeutic units typically do not exceed 20 mA at voltages which may range above 150 kV. When an x-ray machine is operated at nominal voltages of 10 to 140 kV, the emitted x-rays provide limited penetration of tissue, and are thus useful in treating skin lesions. At higher voltages (approximately 250 kV), deep x-ray penetration is achieved, which is useful in the treatment of major body tumors. Super voltage machines, operable in the 4 to 8 megavolt (MV) region, are used to ablate or destroy all types of tumors, except superficial skin lesions.

A conventional x-ray tube includes an anode, grid, and cathode assembly. The cathode assembly generates an electron beam which is directed to a target, by an electric field established by the anode and grid. The target in turn emits x-ray radiation in response to the incident electron beam. The radiation absorbed by a patient generally is that which is transmitted from the target in the x-ray tube through a window in the tube, taking into account transmission losses. This window typically is a thin section of beryllium, or other suitable material. In a typical x-ray machine, the cathode assembly consists of a thoriated tungsten coil approximately 2 mm in diameter and 1 to 2 cm in length which, when resistively heated with a current of 4 amps (A) or higher, thermionically emits electrons. This coil is surrounded by a metal focusing cup which concentrates the beam of electrons to a small spot on an opposing anode which also functions as the target. In models having a grid, it is the grid which both controls the path of the electron beam and focuses the beam.

The transmission of an electron beam from cathode to anode is influenced by electron space charge forces which tend to become significant in conventional x-ray machines at currents exceeding 1 A. In such conventional machines, the beam is focused on the anode to a spot diameter ranging anywhere from 0.3 to 2.5 millimeters (mm). In many applications, most of the energy from the electron beam is converted into heat at the anode. To accommodate such heating, high power medical x-ray sources often utilize liquid cooling and a rapidly rotating anode, thereby establishing an increased effective target area, permitting a small focal spot while minimizing the effects of localized heating. To achieve good thermal conductivity and effective heat dissipation, the anode typically is fabricated from copper. In addition, the area of the anode onto which an electron beam is incident requires a material of high atomic number for efficient x-ray generation. To meet the requirements of thermal conductivity, effective heat dissipation, and efficient x-ray generation, a tungsten alloy typically is embedded in the copper.

In use, the total exposure from an x-ray source is directly proportional to the time integral of the electron beam. During relatively long exposures (e.g. lasting 1 to 3 seconds), the anode temperature may rise sufficiently to cause it to glow brightly, accompanied by localized surface melting and pitting which degrades the radiation output. However, thermal vaporization of the tube's coiled cathode filament is most frequently responsible for conventional tube failure.

While the efficiency of x-ray generation is independent of the electron beam current, it is highly dependent on the acceleration voltage. Below 60 kV, only a few tenths of one percent of the kinetic energy from an electron is converted to x-rays, whereas at 20 MV that conversion factor rises to 70 percent. An emitted x-ray spectrum is composed in part of discrete energies characteristic of transitions between bound electron energy levels of the target element. The spectrum also includes an x-ray energy continuum, known as bremsstrahlung, which is caused by acceleration of the beam electrons as they pass near target nuclei. The maximum energy of an x-ray cannot exceed the peak energy of an electron in the beam. Further, the peak of the bremsstrahlung emission curve occurs at approximately one-third the electron energy.

Increasing the electron current results in a directly proportional increase in x-ray emission at all energies. However, a change in beam voltage results in a total x-ray output variation approximately equal to the square of the voltage, with a corresponding shift in peak x-ray photon energy. The efficiency of bremsstrahlung radiation production increases with the atomic number of the target element. The peak output in the bremsstrahlung curve and the characteristic spectral lines shift to higher energies as the atomic number of the target increases. Although tungsten ($Z=74$) is the most common target material used in modern tubes, gold ($Z=79$) and molybdenum ($Z=42$) are used in some specialty tubes.

X-rays interact in several ways with matter. For biological samples, the following two types of interactions are most important: Compton scattering of moderate-energy x-rays with outer shell electrons; and, photoionizing interactions of inner shell electrons. In these processes, the probability of atom ionization decreases with increasing photon energy in both soft tissue and bone. For the photoelectric effect, this relationship follows an inverse third-power law.

One disadvantage of present x-ray devices used for therapy is the high voltage required when directed to soft tissue within or beneath bone. One example is in directing x-rays to areas of the human brain, which is surrounded by bone. High energy x-rays are required to penetrate the bone, but often damage the skin and brain tissue. Another example in radiation therapy is in directing the x-rays to soft tissue located within the body cavity, couched among other soft tissue, or within an internal calciferous structure. Present high-voltage machines are limited in their ability to selectively provide desired x-ray radiation to such areas.

Another disadvantage of the high voltage output of present x-ray sources is the damage caused to skin external to the affected organ or tissue. Therefore, high voltage devices of present systems often cause significant damage not only to the target region or tissue, but also to all surrounding tissue and surface skin, particularly when used for human tumor therapy. However, since present devices apply x-ray radiation to target regions internal to a patient from a source external to the target region, such incidental tissue damage is practically unavoidable.

Specifically as to brain tissue, which lacks any substantial regenerative ability, the treatment of brain tumors requires precise techniques to bring about specific tissue destruction. The use of conventional x-ray devices in brain tumor therapy often lacks the precision needed in volumetric irradiation, resulting in the damage of non-cancerous tissue of the brain and associated glandular structures.

An alternative form of tumor therapy, called brachytherapy, involves implanting encapsulated radioisotopes in or near the tumor to be treated. While such use of radioisotopes may be effective in treating certain types of tumors, introduction of the isotopes requires invasive procedures which have potential side-effects, such as the possibility of infection. Moreover, brain swelling may occur in some applications because the emission from the isotope cannot be controlled. Further, there is no ability to provide selective control of time dosage or radiation intensity. Handling and disposal of such radioisotopes involves hazards to both the individual handler and the environment.

Invasive techniques of the brain require precise control of irradiation through the choice and concentration of isotopes used. Intracranial penetration poses a significant risk as is well known in the art.

In view of the above requirements and limitations to the use of x-rays from present machines in therapeutic, diagnostic, palliative, or evaluative environments, there remains a need for a relatively small, easily manipulated, controllable, low-energy, x-ray device where the x-ray source can be positioned in proximity to the environment to be irradiated. Such a device operating at low energy and power will be suitable for many of the applications described herein.

Thus, it is an object of the present invention to provide an easily manipulated, low-power x-ray device.

It is another object of the invention to provide a relatively small, low-power x-ray device having a controllable, or programmable, power supply.

It is another object of the invention to provide a relatively small, low-power x-ray device which is implantable into a patient for directly irradiating a desired region of tissue with x-rays.

It is another object of the invention to provide a low-power x-ray device for irradiating a volume to establish an absorption profile defined by predetermined isodose contours in order to reduce tissue damage outside the desired irradiation region.

It is yet another object of the invention to provide a relatively small, surface-mountable, low-power x-ray device for affecting a desired surface region with x-rays.

It is yet another object of the invention to provide a relatively small, low-power x-ray device which is insertable into a patient for directly irradiating a specified region with x-rays.

It is yet another object of the invention to provide a small, low-power x-ray device for use with a reference frame assembly for controllably positioning an x-ray source adjacent to or within a tumor in a patient in order to irradiate and therefore treat that tumor.

It is yet another object of the invention to provide a small, low power x-ray device which can be threaded through existing, irregularly shaped passageways.

It is yet another object of the invention to provide a small, low power x-ray device which includes an improved mechanism for directing an electron beam at a target element.

SUMMARY OF THE INVENTION

Briefly, the invention is an easily manipulated apparatus having a low-power, electron beam (e-beam) activated x-ray source of preselected, or adjustable, duration, effective energy and intensity. In medical applications, the apparatus (or "probe") may be fully or removably inserted into, implanted into, or surface-mounted onto a desired area of a patient to irradiate a region with x-rays. Additionally, the apparatus can be assembled with a variable-thickness x-ray shield to allow irradiation of, and consequent absorption in, a preselected volume, defined by a set of isodose contours, so as to reduce the destructive effects of x-rays outside the desired irradiation region. The apparatus can be assembled in combination with a reference frame, for example, a stereotactic frame, and an associated coupler for use in the treatment of brain tumors. The apparatus is also useful for treating other tumors, such as may be found in the breast or liver or other places; also, the apparatus may be used to treat cancer cells on the surface of body cavities, such as the bladder.

The apparatus operates at a relatively low voltage, for example, in the range of approximately 10 kV to 90 kV, with small electron currents, for example, in the range of from approximately 1 nA to 100 $\mu$A. To achieve a desired radiation pattern over a desired region, while minimally irradiating other regions, x-rays are emitted from a nominal, or effective "point" source located within or adjacent to the desired region-to-be-irradiated. Preferably, the point source is used together with a mask, or shield, to control the shape of the emitted x-radiation. In some applications, a low dose rate of x-rays irradiates any part of the desired region, either continually or periodically, over extended periods of time. For use with a reference frame for treatment of brain tumors, a high dose rate for single dose irradiation is generally preferred. With the use of a "repeat localizer," the single dose can be replaced, if desired, by a series of high dose rate, i.e., fractionated, treatments.

The apparatus includes a controllable, or programmable, power supply located outside the desired region-to-be-irradiated to enable variations in voltage, current, and timing of an electron beam. The electron beam is controlled to pass along a desired beam axis and to be incident on a target which is preferably located in the patient's body, although for irradiation of surface of the body, the beam axis and target are extra-corporeal. The axis may be straight, or curved. The composition and/or geometry of the target, or x-ray emitting, material is selected to provide a customized pattern of x-rays. Shielding at the target, or around the target, further enables control of the energy and spatial profile of the x-ray emission to closely match the desired distribution of radiation throughout the desired region. A stable and reproducible source of x-rays can be created with the electron spot either larger or smaller than the target, although the former results in an inefficient use of electrons and the latter may compromise the spherical isotropy of the emitted radiation.

The present invention further provides a method of treating malignant cells, such as found in tumors, in vivo, utilizing the apparatus described above. Generally, the method involves identifying and locating malignant cells with a device generally available in the art, such as by computed tomography (CT) scanning or magnetic resonance imaging (MRI). A needle-type biopsy of the tumor may be performed to confirm the diagnosis. Then the region of treatment is selected and the radiation dosage determined. Such radiation treatment planning involves defining the size and shape of the tumor determining precisely its location in the body, identifying radiation-sensitive critical biological structures surrounding the tumor, deciding on the proper radiation dose distribution in the tumor and surrounding tissue and the entry path in to the tumor of the implanted portions of the apparatus. For spherical tumors, treatment planning can be performed manually using CT or MRI data. However, for more complex geometries, close-by critical structures, or higher precision procedures, computer-based "3-D" imagery is preferred. In that case, tumors and critical structures are, for example, manually or semiautomatically segmented on a series of digitized CT scans, and a 3-D composite is rendered, which allows viewing the tumor from any direction. Various software systems have been developed for radiosurgical procedures, such as those using the linac and gamma knife, and some are commercially available. For example, Radionics Software Applications of Arlington, Mass. offers for sale software which images the CRW and BRW stereotactic frame affixed to a graphically transparent skull. Isodose profiles are overlaid on the tumor and other brain tissue. Similar software may be used with the invention disclosed in U.S. patent application Ser. No. 955,494 which effects imaging with respect to a stereotactic frame, for use with the x-ray-radiating electron beam target imbedded in the tumor. Isodose contours around the target are superimposed on the tumor and adjacent tissue. The absolute radiation dosage delivered along each contour is determined by experimental dosimetry performed to calibrate the probe. In these tests, the dose is measured at multiple locations around the target immersed in a water tank. Soft tissue is adequately simulated by water. The dose is measured by an ionization chamber, such as is manufactured by PTW of Freiburg, Germany, wherein x-ray generated ions create a small current which is detected by an electrometer, such as is commercially available from Keithley Radiation Measurement Division in Cleveland, Ohio. Alternatively, the target can be immersed in a biological tissue-simulating phantom. Such plastic, "solid water," phantoms are commercially available (RMI, Middleton, Wis.) and simulate various body tissues, e.g., soft tissue of the brain. Either thermoluminescent detectors (TLD) or calibrated x-ray sensitive film (e.g., gafchromic film from Far West Technologies, Goleta, Calif.) can be positioned in the solid water to measure the dose directly. Using the imaging and dosimetry results from the radiation treatment planning, a low-power electron beam source and a selectively shaped x-ray radiation pattern generating target and shield assembly are positioned within or proximal to a region containing the cells to-be-irradiated, generally tumor cells, for example, in conjunction with a stereotactic frame assembly, such as disclosed in U.S. patent application Ser. No. 955,494. Other positioning assemblies, or methods, may be used.

Pursuant to the present invention, the target and shield assembly geometry and materials are shaped and selected in accordance with the characteristics of the desired region-to-be-irradiated. A programmable power supply is provided, which may be used to vary the voltage, current, and duration of the electron beam source to establish, in accordance with dosimetry information, a desired electron beam which is directed to the target. Finally, x-radiation emitted from the target, as modified by the shield assembly, is propagated through the desired region-to-be-irradiated for destruction of the cells in that region. By use of a method of signal feedback, in which the x-rays emitted from the target in an backward direction along the path of the electron beam are monitored by a detector positioned behind the electron emitter, adjustments in the deflection of the electron beam can be made to automatically control and optimally position the electron beam region of incidence, or spot, on the target.

In particular, the treatment of a brain tumor can be carried out utilizing an apparatus of the present invention comprising the combination of a low-power x-ray source for generation of a controllable irradiation pattern, with a device for accurately positioning the x-ray source in the brain. The x-ray source can thus be precisely located near or in the tumor.

The x-ray source, together with the target and shield assembly, of the present invention may be used in various body locations to generate custom-designed irradiation fields for treatment of a variety of types of tumors. Also, irradiation fields can be customized for each tumor treated. However, geometrical similarities for many tumors will allow this treatment with a standard set of shields.

According to a further embodiment of the invention, the probe can be flexible in nature to allow it to be threaded down existing passageways or around obstacles. According one such embodiment, a photoemissive element (i.e. a photocathode) is located, along with a target element, in the target assembly. Additionally, a flexible fiber optical cable, which couples light from a laser source to the photocathode, can form the basis for the flexible probe.

One terminal of a high voltage power supply is coupled to the photocathode, via an electrical conductor embedded in the fiber optical cable. The other terminal of the power supply is coupled to the target element, via an electrically conductive, flexible, outer sheath formed around on the fiber optical cable. In this way, an electrical field is established which acts to accelerate electrons emitted from the photocathode toward the target element. As in previously discussed embodiments, the target element emits x-rays in response to incident electrons from the photocathode.

BRIEF DESCRIPTION OF DRAWINGS

The foregoing and other objects of this invention, the various features thereof, as well as the invention itself, may be more fully understood from the following description, when read together with the accompanying drawings in which:

FIG. 8A is a cross-section view of the assembly of FIG. 8, taken along lines 8a;

FIG. 9 is a perspective view of a brain tumor x-ray treatment system incorporating a stereotactic frame for positioning the x-ray source;

FIGS. 15A and 15B are perspective views of a probe and target assembly for accurate angular alignment of an x-ray shield;

FIGS. 16 is a cross-sectional view of a low power x-ray source having an internal beam steering assembly which includes a feedback loop for electron beam positioning;

Like numbered elements in each FIGURE represent the same or similar elements.

DESCRIPTION OF THE PREFERRED EMBODIMENTS

The present invention is a relatively small, electron-beam activated, low power x-ray apparatus. The apparatus may be used for medical purposes, for example, therapeutic or palliative radiation treatment of tumors, or for other purposes.

With particular regard to medical uses, the apparatus may be fully implanted or partially inserted into a preselected internal region of a patient to provide x-ray radiation over selected exposure times. Alternately, the apparatus may be mounted on a surface of a patient external to a region to be irradiated. Also disclosed is a method for treating tumors in a patient, using the apparatus of the invention.

Generally, the apparatus of the present invention includes an electron-beam (e-beam) activated x-ray source which operates at relatively low voltages, i.e. in the range of approximately 10 kV to 90 kV, and relatively small electron beam currents, i.e. in the range of approximately 1 nA to 100 µA. At those operating voltages and currents, the x-ray output is relatively low, and the apparatus may be made quite small and be adapted for implantation in medical therapeutic applications. In view of the low level x-ray output, adequate tissue penetration and cumulative dosage may be attained by locating the x-ray source adjacent to or within the region to be irradiated. Thus, the x-rays are emitted from a well-defined, small source located within or adjacent to the region to be irradiated. In one embodiment, a low dose rate of x-rays may be applied to any part of a tumor, either continually or periodically, over extended periods of time, e.g., up to one month. In use with a stereotactic frame for the treatment of brain tumors, a higher dose rate may be applied to a tumor for shorter periods of time (i.e., on the order of 5 minutes to 3 hours).

The present invention provides interstitial radiotherapy similar to that achieved with implanted capsules, needles, tubes, and threads containing natural or artificial radioactive isotopes, known as brachytherapy. However, a programmable power supply may be included in the x-ray source of the present apparatus to vary energy, intensity, and duration of the radiation. This differs from brachytherapy in that the intensity and penetration depth of the x-rays may be changed without surgically or invasively replacing the isotopes. Furthermore, the present invention is not limited by the half-life of a particular isotope, and does not pose a radiation hazard when turned off.

Figure 1:
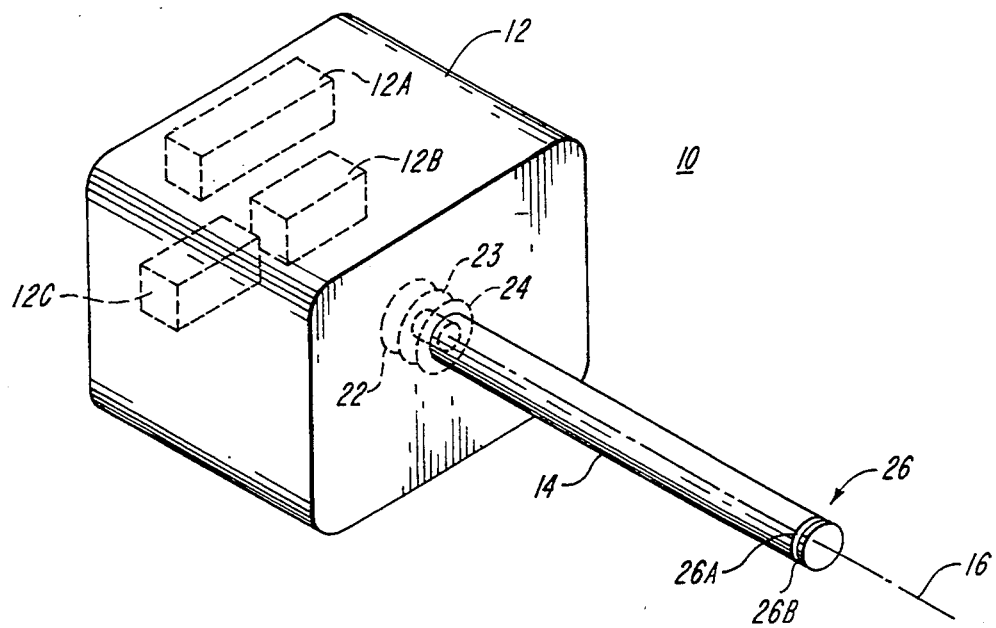
FIG. 1 is a perspective view of a low power x-ray source embodying the present invention.

FIG. 1 shows an x-ray apparatus 10 embodying the present invention. Apparatus 10 includes a housing 12 and an elongated cylindrical probe 14 extending from housing 12 along a reference axis 16. The housing 12 encloses a high voltage power supply 12A (illustrated in electrical schematic form in FIGS. 6 and 7). The probe 14 is a hollow tube having an electron beam generator (cathode) 22 adjacent to the high voltage power supply 12A. Cathode 22 is located in close proximity to an annular focusing electrode 23 typically at nearly the same potential as the cathode 22. An annular anode 24 is positioned approximately 0.5 cm or more from the annular focusing electrode 23. A hollow, tubular probe 14 extends along the same axis as the cathode, grid, and the hole in the anode. Probe 14 is integral with the housing 12 and extends toward a target assembly 26. In various embodiments, parts of the probe 14 may be selectively shielded to control the spatial distribution of x-rays. In addition, the probe 14 may be magnetically shielded to prevent external magnetic fields from deflecting the beam away from the target.

The electron beam generator 22 may include a thermionic emitter (driven by a floating low voltage power supply) or a photocathode (irradiated by an LED or laser source). The high voltage power supply establishes an acceleration potential difference between the cathode of generator 22 and the grounded anode 24 so that an electron beam is established along the reference axis 16, through the center hole of the anode and to the target assembly 26, with the region between anode 24 and the target assembly 26 being substantially field free. The beam generation and acceleration components are adapted to establish a thin (e.g. 1 mm or less in diameter) electron beam within the probe 14 along a nominally straight axis 16.

In a preferred embodiment, the probe 14 is a hollow, evacuated cylinder made of a beryllium (Be) cap and a molybdenum-rhenium, (Mo-Re), molybdenum (Mo) or mu-metal body and a stainless-steel base extension. The cylinder is 16 cm long, with an interior diameter of 2 mm, and an exterior diameter of 3 mm. The target assembly 26 includes an emission element consisting of a small beryllium (Be) target element 26A coated on the side exposed to the incident electron beam with a thin film or layer 26B of a high-Z element, such as tungsten (W), uranium (U) or gold (Au). By way of example, with electrons accelerated to 30 keV-, a 2.2 micron thick tungsten film absorbs substantially all the incident electrons, while transmitting approximately 95% of any 30 keV-, 88% of any 20 keV-, and 83% of any 10 keV-x-rays generated in that layer. In the preferred embodiment, the beryllium target element 26a is 0.5 mm thick with the result that 95% of these x-rays generated in directions normal and toward the substrate, and having passed through the tungsten target, are then transmitted through the beryllium substrate and outward at the distal end of probe 14. While the target element 26A shown in FIG. 3B is in the form of a disc, other shaped elements may be used, such as those having hemispherical or conical outer surfaces.

In some forms of the target, the window element 26A may include a multiple layer film (or alloy) 26B, where the differing layers may have different emission characteristics. By way of example, the first layer may have an emission (vs. energy) peak at a relatively low energy, and the second (underlying) layer may have an emission (vs. energy) peak at a relatively high energy. With this form of the invention, a low energy electron beam may be used to generate x-rays in the first layer (to achieve a first radiation characteristic) and high energy electrons may be used to penetrate through to the underlying layer (to achieve a second radiation characteristic). As an example, a 0.5 mm wide electron beam is emitted at the cathode and accelerated to 30 keV- through the anode, with 0.1 eV transverse electron energies, and arrives at the target assembly 26 sixteen centimeters downstream from the anode, with a beam diameter of less than 1 mm at the target element 26A. X-rays are generated in the target assembly 26 in accordance with preselected beam voltage, current, and target element 26A composition. The x-rays thus generated pass through the beryllium target element 26A in the probe with minimized loss in energy. As an alternative to beryllium, the target element 26A may be made of carbon or other suitable material which permits x-rays to pass with a minimum loss of energy. An optimal material for target element 26A is carbon in its diamond form, since that material is an excellent heat conductor. Using these parameters, the resultant x-rays have sufficient energy to penetrate into soft tissues to a depth of a centimeter or more, the exact depth dependent upon the x-ray energy distribution.

The apparatus of FIG. 1 is particularly adapted for full implantation into a patient, where the housing 12 has a biocompatible outer surface and encloses both a high voltage power supply circuit 12A for establishing a drive voltage for the beam generator 22, and an associated battery 12B for driving that circuit 12A. In this case, an associated controller 12C establishes control of the output voltage of the high power supply circuit 12A, in the manner described below.

The apparatus of FIG. 1 may also be used in a manner where only the probe 14 is inserted into a patient while the housing remains outside the patient, i.e., a transcutaneous form. In the latter form, some or all of the various elements shown within housing 12 may alternatively be remotely located.

Figure 2:
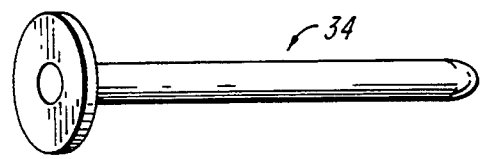
FIG. 2 is a schematic representation of a sheath adapted for use with the apparatus of FIG. 1.

In the transcutaneous form, the apparatus 10 may be used with an elongated closed end (or cup-shaped) sheath 34, as shown in FIG. 2, having a biocompatible outer surface, for example, fabricated of medical grade aliphatic polyurethane, as manufactured under the trademark Tecoflex ® by Thermedics, Inc., Woburn, Mass. With this configuration, the probe 14 is first inserted into the sheath 34. The sheath 34 and probe 14 are then inserted into the patient through the skin. Alternatively, a port may be inserted through the skin and attached to it, as for example a Dermaport ® port manufactured by Thermedics Inc., Woburn, Mass. The probe 14 is then inserted into the port.

The lining of the sheath or port can be configured as an x-ray shield by introducing barium sulfate or bismuth trioxide, or other x-ray shielding materials, into the sheath. If necessary, the probe 14 and housing 12 can be secured to the patient's body to prevent any relative motion during the extended time of treatment. An exemplary sheath 34 is shown in FIG. 2.

In one embodiment of the apparatus as shown in FIG. 1, the main body of the probe 14 can be made of a magnetically shielding material such as a mu-metal. Alternatively, the probe 14 can be made of a non-magnetic metal, preferably having relatively high values for Young's modulus and elastic limit. Examples of such material include molybdenum, rhenium or alloys of these materials. The inner or outer surface of probe 14 can then be coated with a high permeability magnetic alloy such as permalloy (approximately 80% nickel and 20% iron), to provide magnetic shielding. Alternatively, a thin sleeve of mu-metal can be fitted over, or inside of, the probe 14. The x-ray apparatus 10 can then be used in environments in which there are dc and ac magnetic fields due to electrical power, the field of the earth, or other magnetized bodies nominally capable of deflecting the electron beam from the probe axis.

In implantable configurations, the power supply 12A and target assembly 26 are preferably enclosed in a metal capsule to prevent current flow from the x-ray source to the patient. The closed housing 12 and probe 14 are, thus, encapsulated in a continuous outer shell of appropriate shielding material such as those mentioned previously.

The high voltage power supply 12A in each of the illustrated embodiments preferably satisfies three criteria: 1) small in size; 2) high efficiency to enable the use of battery power; and 3) independently variable x-ray tube voltage and current to enable the unit to be programmed for specific applications. A high-frequency, switch-mode power converter is used to meet these requirements. The most appropriate topology for generating low power and high voltage is a flyback voltage converter working in conjunction with a high voltage, Cockroft-Walton-type multiplier. Low-power dissipation, switch-mode power-supply controller-integrated circuits (IC) are currently available for controlling such topologies with few ancillary components.

In order to provide active control of the x-rays, a preferred embodiment of the present invention establishes independent control of cathode voltage and current without the use of a grid electrode. In that form of the invention, an radio frequency ohmic heating current is provided to a thermionic cathode 22, preferably using a transformer-coupled 0.6 volt, 0–300 mA filament power supply floating at the cathode potential of 40 kV.

Figure 3A:
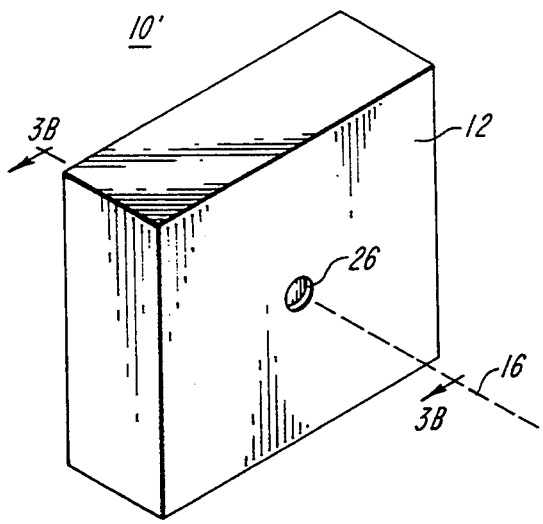
FIGS. 3A and 3B are a perspective view and sectional view, respectively, of a surface-mountable apparatus embodying the present invention.
Figure 3B:
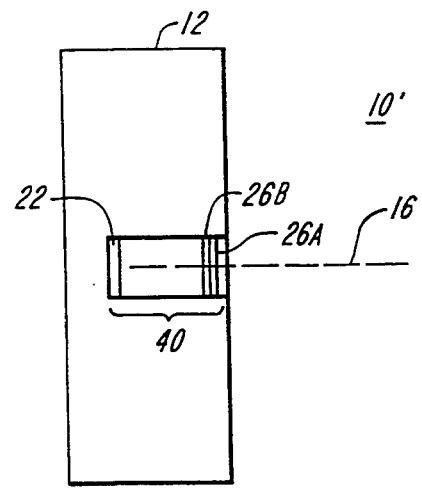

FIGS. 3A and 3B show an alternative embodiment 10' of the invention adapted for superficial usage, that is for direct placement on the skin of a patient. This form of the invention is particularly useful for x-ray treatment of skin lesions or tumors, or other dermatological applications. In FIGS. 3A and 3B, elements that correspond to elements in the embodiment of FIG. 1 are denoted with the same reference designations. Apparatus 10' generates an electron beam in a channel 40 enclosed within housing 12, where that channel 40 corresponds to probe 14. In the present embodiment, of FIGS. 3A and 3B, the target assembly 26 (elements 26A and 26B) functions as the anode as well as an x-ray emitter. Otherwise, the apparatus 10' is similar to apparatus 10. As with the configuration of FIGS. 3A and 3B, low power x-rays may be directed to a desired skin region of a patient.

In all of the above-described embodiments, the x-ray emission element of the target assembly is adapted to be adjacent to or within the region to be irradiated. The proximity of the emission element to the targeted region, e.g. the tumor, eliminates the need for the high voltages of presently used machines, to achieve satisfactory x-ray penetration through the body wall to the tumor site. The low voltage also concentrates the radiation in the targeted tumor, and limits the damage to surrounding tissue and surface skin at the point of penetration. For example, the delivery of 4000 rads, as is required after a mastectomy, with a 40 kV, 20 µA electron beam, may require approximately 1 to 3 hours of radiation. However, since the x-ray source is, in this preferred embodiment, insertable proximate to, or into, the region-to-be-irradiated risk of incidental radiation exposure to other parts of the patient's body is significantly reduced.

Further, specificity in treating tumors may be achieved by tailoring the target and shield geometry and material at the emission site. This tailoring facilitates the control of energy and the spatial profile of the x-ray emission to ensure more homogenous distribution of the radiation throughout the targeted tumor.

Figure 4:
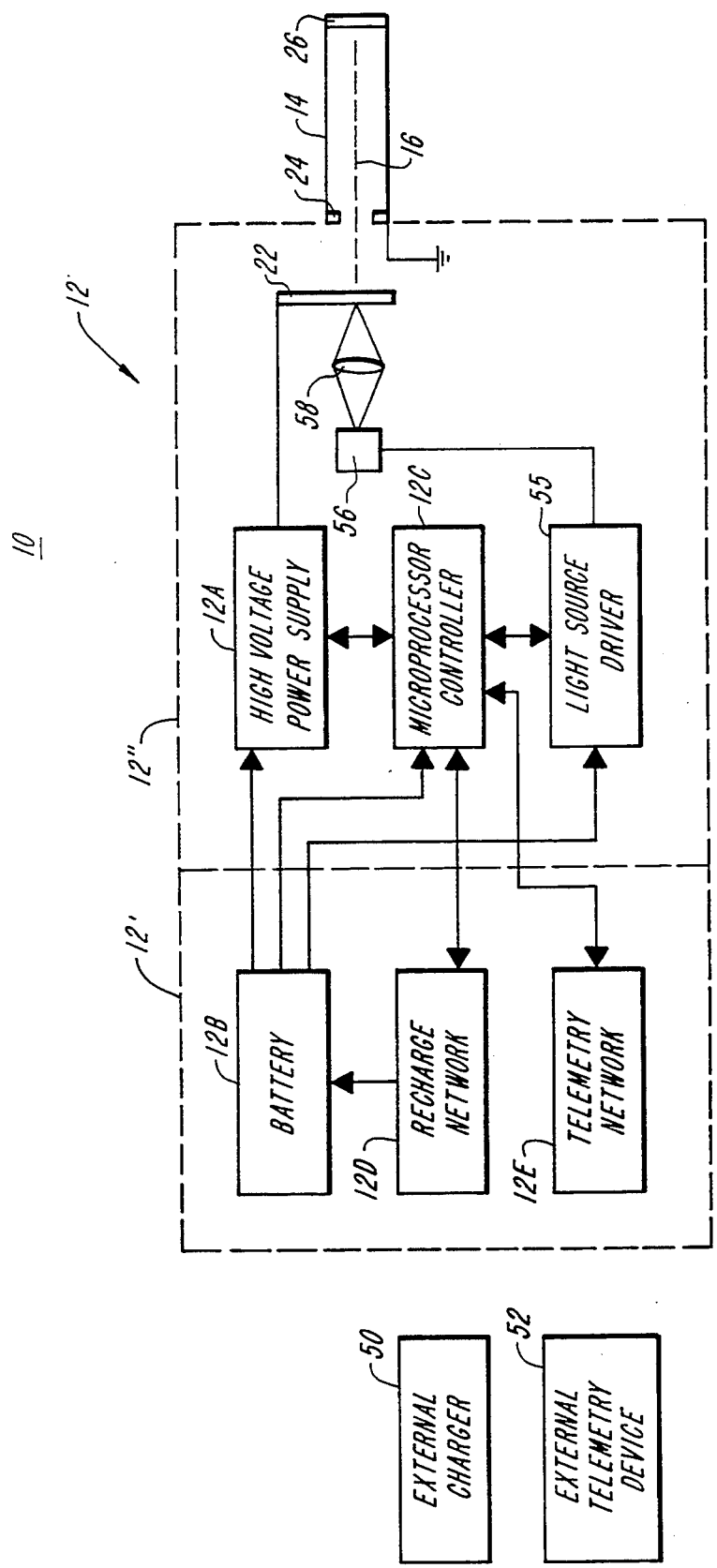
FIG. 4 is a schematic block diagram of the embodiment of FIG. 1.

FIG. 4 is a schematic representation of the x-ray source apparatus 10 shown in FIG. 1. In that preferred configuration, the housing 12 is divided into a first portion 12' and a second portion 12". Enclosed within the first housing portion 12' is a rechargeable battery 12B, a recharge network 12D for the battery 12B, which is adapted for use with an external charger 50, and a telemetry network 12E, adapted to be responsive to an external telemetry device 52 to function in the manner described below. That portion 12' is coupled by cables to the second housing portion 12". The second housing portion 12" includes the high voltage power supply 12A, controller 12C and the probe 14, as well as the electron beam generating element 22. In one embodiment, the electron beam generator includes a thermionic emitter 22 driven by the power supply 12A. In operation, power supply 12A heats the thermionic emitter 22, which in turn generates electrons which are then accelerated toward the anode 24. The anode 24 attracts the electrons, but passes them through its central aperture toward the target assembly 26. The controller 12C controls the power supply 12A to dynamically adjust the cathode voltage, the electron beam current, and temporal parameters, or to provide pre-selected voltage, beam current, and temporal parameters.

Also illustrated, is an alternative electron beam generator which includes a photoemitter 22 irradiated by a light source 56, such as a diode laser or LED, powered by a driver 55. The light is focused on the photoemitter 22 by a focusing lens 58.

In the illustrated embodiment, device 52 and network 12E cooperate to permit external control (dynamic or predetermined) control over the power supply 12A and temporal parameters. In embodiments when the housing 12" is not implanted, but where only probe 14 extends into a patient's body, the controller 12C may directly be used to control operation; in that case there is no need for network 12E.

Figure 5A:
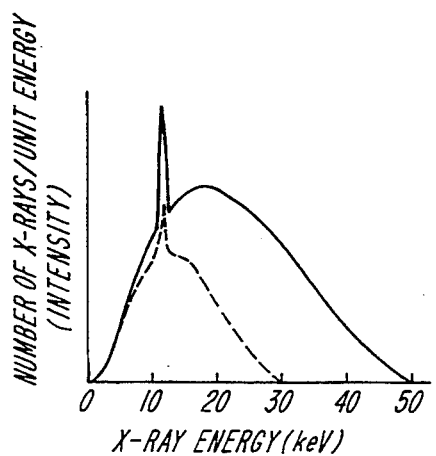
FIGS. 5A and 5B are graphical representations of the x-ray emission spectrum of tungsten- and molybdenum-targets, respectively.
Figure 5B:
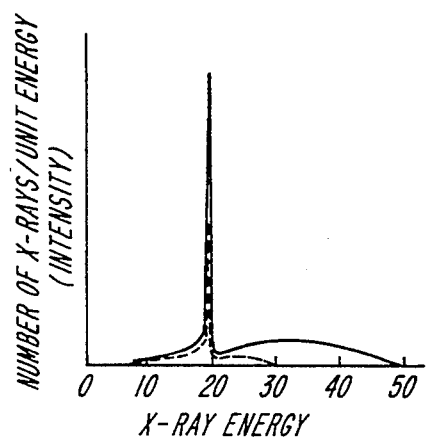

In an important aspect of the invention, the target assembly 26 may be shaped to emit x-rays in a radiation pattern in a predetermined spectral range, and having a predetermined spatial distribution. This spectral target shaping may be achieved in part by selecting target materials of known characteristics. For example, as shown in FIGS. 5A and 5B, the emission spectra for tungsten targets (FIG. 5A) and molybdenum targets (FIG. 5B) are distinct. FIG. 5A shows the x-ray emission spectrum from a tungsten target tube operating at 30 and 50 kV. Note that the bremsstrahlung spectrum predominates, and that x-rays are supplied in a wide energy range. FIG. 5B shows the emission spectrum from a molybdenum target tube, also operating at 30 and 50 kV. Note the near absence of bremsstrahlung x-rays. Note also that the change in tube potential from 30 to 50 kV results in a minor change in the shape of the emission spectrum from a molybdenum target x-ray tube. Thus, the x-ray spectral emission from target assembly 26 may effectively be shaped by selecting the target material to provide the desired radiative penetration of tissue, e.g., the tumor.

The x-ray spatial distribution may be also shaped by altering the geometric configuration of target element 26A. By way of example, the target element 26A may be shaped such that the electrons directed from the anode will be incident at a predetermined angle or may be selectively directed to different areas of the region from which emission is to occur. By way of further example, the target element 26A can be fabricated to be thick enough to be substantially opaque to electrons but thin enough to be substantially transparent to x-rays. More specifically, if a spherical gold target element having a thickness of 0.5 μm and a 40 kV electron beam is employed, substantially all of the electrons are stopped by the target element and substantially all of the x-rays generated in the target element can escape.

Figure 12:
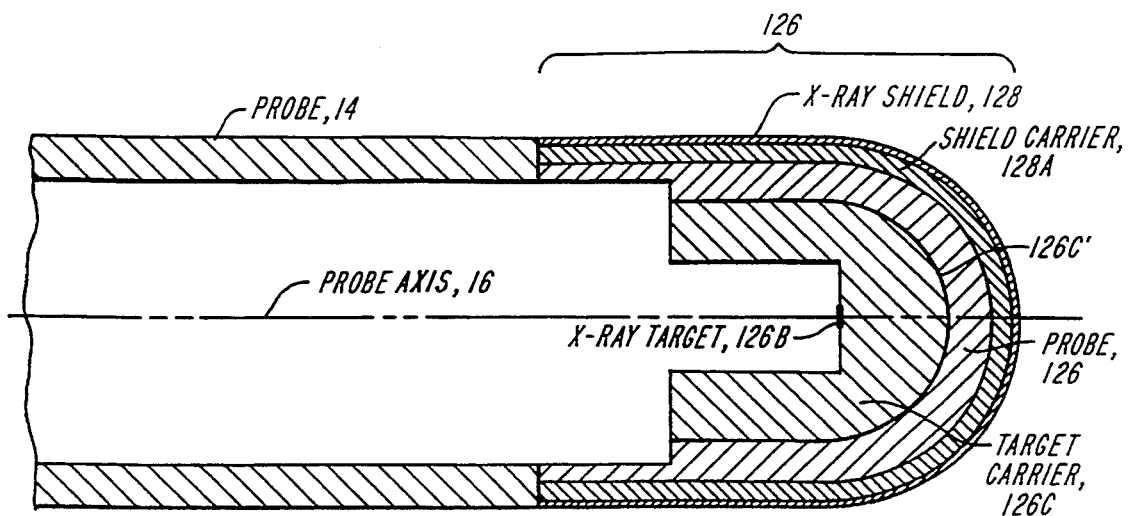
FIG. 12 is a cross-sectional view of the end of a probe having an alternate target assembly which includes an x-ray shield and x-ray target for producing a stable and reproducible source of x-rays.

The x-ray spatial distribution can also be shaped by incorporating an x-ray transmissive shield, having a variable thickness profile, into the target assembly 26. FIG. 12 shows a probe 14 having an alternate target assembly 126, for use with the x-ray apparatus 10 shown in FIG. 1, which incorporates such a shield. In the illustrative embodiment, the probe 14 is substantially similar to the probe 14 shown in FIG. 1, except for the target assembly 126. Target assembly 126 includes a probe tip 126A made of a material (e.g. Be) which is nearly transparent to x-rays, and an x-ray target 126B for generating a source of x-rays upon irradiation with an electron beam, attached to the probe 14 along a probe axis 16 at the end distal to the cathode 22 and anode 24 (shown in FIG. 1). In the preferred form, the outer surface of the probe tip 126A is convex, and preferably hemispherical, as in the illustrated embodiment, although other convex shapes can be used. The target assembly 126 is fabricated such that the outer diameter of the probe tip 126A is less than the outer diameter of the probe 14. A variable thickness x-ray shield (or shadow mask) 128 and an underlying shield carrier 128A are positioned over the probe tip 126A of the target assembly 126. At the junction of the target assembly 126 and probe 14, the outer diameter of the target assembly 126 substantially matches that of probe 14.

The x-ray shield 128 is made from a material which has a high attenuation factor, and is supported by the shield carrier 128A. The x-ray flux from any point of the target assembly 126 is dependent in part upon the thickness of the x-ray shield 128 along an axis extending from the target 126B and passing through that point. Thus, in accordance with the invention, a selective restriction in thickness of the x-ray shield 128 is used to generate spatially-variable x-ray dose distributions.

In a preferred embodiment, the probe 14 has an outer diameter of 3 mm and an inner diameter of 2 mm, and is typically 10 to 16 cm long. The target carrier 126C is made of beryllium and has a hemispherical tip 126C' with a radius 0.8 mm, the probe tip 126A is made of beryllium and has a thickness 0.5 mm. The shield carrier 128A is made of a light element, such as beryllium, magnesium, aluminum, or carbon and has a thickness 0.2 mm, and the shield 128 has a thickness in the range 0 to 0.1 mm if made of gold.

The x-ray target 126B is a small disk (e.g., 0.1 mm diameter) of an x-ray emissive material (e.g., a metal with a high atomic number such as gold) deposited in the center of the target carrier 126C. As will be discussed in further detail below, the size of the x-ray target 126B may be small relative to the diameter of the electron beam established along the probe axis 16, so that the source of x-rays produced is defined by the position of the small target and not by the position or size of the electron beam. This feature permits illumination of the x-ray shield 128 with a reproducible and stable source of x-rays. However, for an electron beam whose spot on the target 126B is larger than the target 126B, there is a loss of efficiency in generating x-rays. Such a loss can be avoided by focusing the beam to a small spot comparable to the size of the target 126B, and controlling its position on the target 126B by suitable means.

The spatial resolution of the preselected irradiation volume which can be obtained by using the shield 128 is limited by several factors, including the penumbra due to the finite size of the x-ray source; the instability of the size and position of the x-ray source due to corresponding instability in the x-ray generating electron spot; the scattering of the x-ray deposited energy in the irradiated volume; and the probe-to-probe reproducibility of the x-ray source and its position relative to the shield 128.

The penumbra is determined by the ratio of the size of the x-ray source to its distance from the shield 128. For a uniform source, a preferable range for this ratio is on the order of 1/20 to ⅓, depending on the scattering behavior. The stability of the size of the x-ray source and its position is preferably a small fraction of the optimum source to distance ratio.

One method of establishing an acceptable penumbra and registration of the shield x-ray source is to control the position and size of the x-ray source by controlling the focus and deflection of the incident electron beam along axis 16. For instance, the electron beam can be focused to a spot on the x-ray emissive surface of target 126B, the diameter of the focal spot thus being the size of the x-ray source. This method requires not only that the spot size be correct, but that the position of the spot relative to the x-ray shield 128 be accurately known and maintained.

In this embodiment, the target can theoretically be as large as fabrication convenience dictates. However, in a preferred embodiment, the x-ray target 126B is substantially the same size or only slightly larger than the electron beam.

In order to ensure that the electron spot position, relative to the shield, is both temporally stable for any given miniature x-ray system and spatially reproducible in all other systems that are in use, accurately placed fiducial marks can be used together with electron beam deflectors to locate the electron spot relative to the shield. Such a fiducial mark consists of an edge, defining a boundary between two regions which have very different behavior in an electron beam. For example, in the present instance, a boundary between the target material 126B, such as Au, and the target carrier material 126C, such as Be, can serve as a fiducial edge. The relevant difference in behavior is that Au is a significantly more efficient x-ray source than Be, when exposed to a high energy electron beam. As the beam passes across the fudiciary mark, an x-ray detector can sense the difference of x-ray intensity and generate a corresponding control signal for application to the beam deflectors.

The x-ray detector can be embedded in a feedback control loop to servo the beam onto the target and preferably, the center of the target, as viewed from the electron source. In one such configuration, where the target position is generally known with respect to the beam path, but it is desired to center the beam path on the target, the beam may first be swept across the target in a first (x) direction which is orthogonal to the beam path. As the beam passes the fiducial edges of the target (for example, as the beam encounters the target during the sweep, and then as the beam leaves the target), the controller identifies the position of the fiducial edges and determines an x-component of a control signal representative of the midpoint between the two fiducial edges in the x-direction sweep. Then the beam is positioned in accordance with that control signal component (i.e. mid-way between the detected x-sweep fiducial edges), and swept in a second (y) direction orthogonal to the x-direction and the beam path. During the y-direction sweep, fiducial edges are detected and a y-component of a control signal is determined which is representative of the mid-point between the two fiducial edges detected during the y-direction sweep. The x- and y-components are then used to control the beam to be centered in the target.

In a case where the target position is not initially known with respect to the beam path, the relative position may be quickly established by raster scanning the beam until the target is encountered in an x-direction sweep, or scan. Then, in response to the detection of fiducial edges in that sweep, a mid-point is determined and the beam is positioned to that mid-point position and then swept in the y-direction, i.e. along the perpendicular bisector of a line connecting the fiducial edges of the identified sweep. In response to detection of fiducial edges in that y-sweep, a y-direction mid-point is determined and control signals representative of the x- and y-direction mid-points are used to center the beam on the target. Although described above for determining the center of a target, other desired reference points on the target may be determined and the beam deflected to be incident on those points.

Another way to establish proper source position, and hence ensure the spatial resolution of a shielded radiation field for all systems, is to use a small x-ray target 126B which is the size of the desired x-ray source. Although, in principle any size electron spot can be used without degrading the spatial resolution of the shielded radiation field, it is desirable to make the spot the same size or smaller than the target 126B in order to maximize the energy conversion for electrons to x-rays and hence reduce the time to treat patients or to perform any other desired task using the shielded x-ray source. In this context, if the spot size is defined such that 90% of the electrons in the spot are contained in the so-defined spot size, then making such a spot equal to the small target size would be optimum in the sense that a smaller spot would not significantly improve the system efficiency. In such a case it may not be desirable to make the spot as small as the target. In any event, the use of a small target ensures that all x-ray probes using a shield to define a radiation field will have substantially the same spatial resolution and position relative to the probe tip.

As shown in FIG. 12, the target carrier 126C fits snugly into the end of the probe tip 126A. In the illustrated embodiment, the x-ray target 126B is deposited on the target carrier 126C before being inserted into the probe tip 126A. In instances where the probe tip 126A has been attached to the body of the probe 14 prior to placement of the x-ray target 126B and target carrier 126C, the target carrier 126C can be fabricated such that inner diameter of the probe 14 is slightly greater than the outer diameter of the target carrier 126C in order to make insertion down the body of the probe 14 easier.

It is generally desirable that the target carrier 126C fit tightly into the probe tip 126A in order to ensure mechanical integrity of the structure. This can be achieved, for instance, by making the pans to "press fit" or by utilizing thermal expansion to clamp the two parts together. In the latter case a cold target carrier 126C (e.g., cooled by liquid nitrogen) is inserted into a relatively hotter (e.g., room temperature) probe tip 126A. As the parts reach thermal equilibrium they firmly clamp together.

In an alternative embodiment, the probe tip 126A can be fabricated to include an integral target carrier. The probe tip 126A is attached to the probe 14 subsequent to the placement of the x-ray target 126B.

The x-ray target 126B should be deposited on the target carrier 126C normal to the probe axis 16, and at the center of the concentric hemispherical surfaces which define the end of the probe tip 126A. This concentricity of placement of the x-ray target 126B greatly simplifies the calculation required to design the variable thickness x-ray shield 128 to give desired x-ray isodose contours. As used herein, the term isodose contour refers to a surface of a three-dimensional volume on which every point experiences the same x-ray absorption per unit mass of tissue.

Since the x-ray target 126B can be deposited on the target carrier 126C before insertion into the probe 14, any of several methods can be used to form an x-ray target 126B at the center of the target carrier 126C. One method of fabricating such an x-ray target 126B is to evaporate a high-atomic-number metal through a shield which is inserted into the cavity in the target carrier. The shield can consist of a disk with a central aperture corresponding to the x-ray target 126B and through which the metal is deposited on the target carrier 126C.

Figure 13:
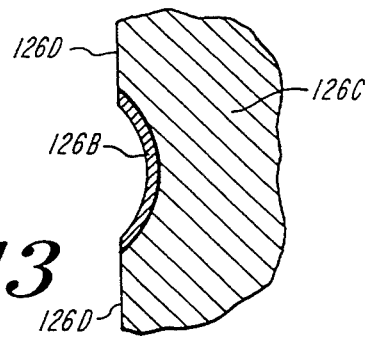
FIG. 13 is a cross-sectional fragmentary view of one geometric form of an x-ray target.

In addition to considerations of x-ray source size and position relative to the x-ray shield 128, it is also necessary to account for x-ray absorption in the x-ray target 126B itself in a direction tangential to the plane of the x-ray target 126B. Such absorption can be reduced by making the x-ray target 126B a curved surface instead of a flat surface. For example, FIG. 13 shows a hemisphere depression in the target carrier 126C which serves to define the form of the x-ray target 126B. The curvature of the x-ray target 126B serves both to reduce the absorption of x-rays in the target and also to spread out any remaining angular dependence of x-rays emitted from the x-ray target 126B. The net result can be a much more isotropic emission of x-rays from the x-ray target 126B which illuminates the x-ray shield 128 located on the shield carrier 128A. The curved target shape shown in FIG. 13 is only one embodiment; other effective shapes may also be used, such as a hemisphere, or a spherical section in combination with a truncated cone.

When the target 126B is deposited in a depression, it can be fabricated with the target carrier 126C in situ within the probe tip 126A, or as an integral part of the probe tip 126A. An evaporative deposition can coat the depression and surrounding surfaces 126D. The high-atomic-weight metal deposited on surfaces 126D can, subsequently be removed by scraping the surface with a flat scraper, which does not contact the depression.

There are applications for the x-ray probe of the present invention which require a broad-area source instead of a point source of x-rays. For example, the resection of a small breast tumor may remove tissue for many centimeters surrounding the focal point of the tumor. Following resection it may be desired to irradiate the "tumor-bed" in order to kill any remaining tumor cells at the periphery of the resection. In a preferred embodiment, in order to reduce tissue damage beyond the desired irradiation volume, the broad-area irradiation is carried out with an x-ray apparatus utilizing an x-ray shield 128 substantially similar to that shown in FIG. 12.

Broad-area radiation can be easily obtained by placing the target assembly 126 of the probe 14 at a distance from the surface to be irradiated. The solid angle of forward radiation from the target assembly 126 can be controlled with an x-ray shield 128. The thickness of the shield 128 at each point is determined so that a substantially uniform radiation pattern is obtained. The target assembly 26 can be employed in a similar fashion.

Figure 19:
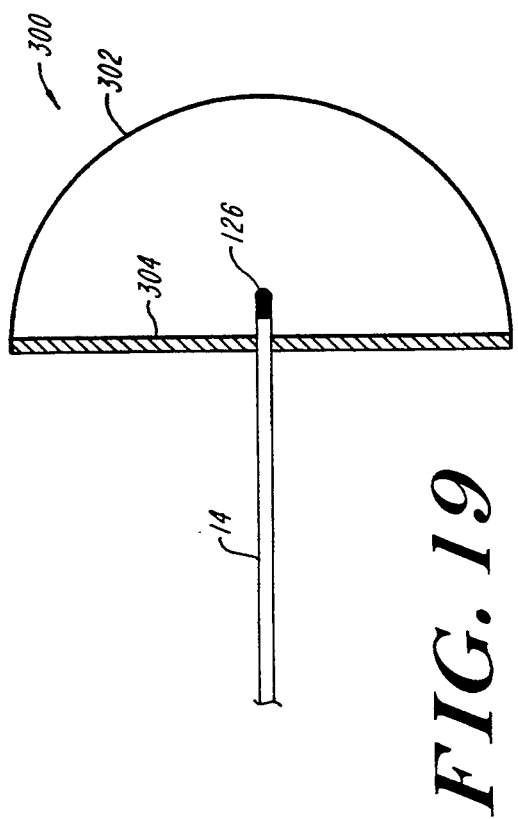
FIG. 19 is a cross-section view of a mechanical probe positioner for broad-area irradiation.

FIG. 19 shows a mechanical positioner 300 for use with an x-ray apparatus of the present invention to achieve the precision required between the target assembly 26 or 126 and the irradiated surface (tissue). The mechanical positioner 300 comprises an interface plate 302 which contacts the tissue, and is made of some material which is transparent to x-rays, such as Be, C, or plastic. The interface plate 302 is attached to the probe 14 by means of an x-ray opaque back plate 304. To further pattern a specific radiation field, the surface of the normally x-ray transparent interface plate 302 can be rendered partially x-ray opaque by way of an x-ray shield in a manner similar to the x-ray shield 128 described above.

Another application for such a broad-area x-ray source is intercavity radiation within the body, such as the inside of the bladder. In such a case the interface plate 302 between the tissue and the broad-area x-ray source can be an inflatable balloon, extending down the probe 14 so that the target assembly 126 is at the center of the balloon. In this case, there would be no opaque backplate 304.

Figure 21A:
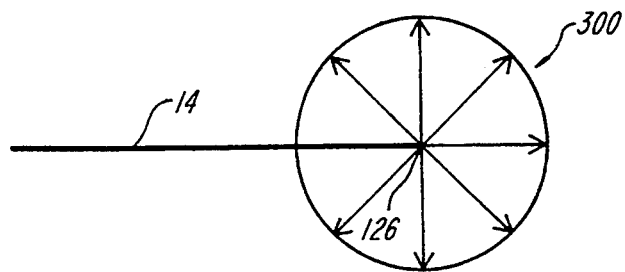
FIGS. 21A–21F show examples of various isodose contours that can be achieved with the invention.
Figure 21B:
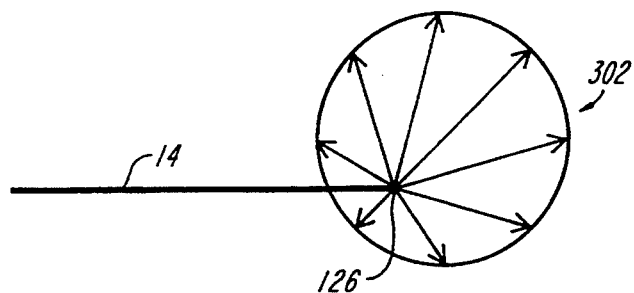
Figure 21C:
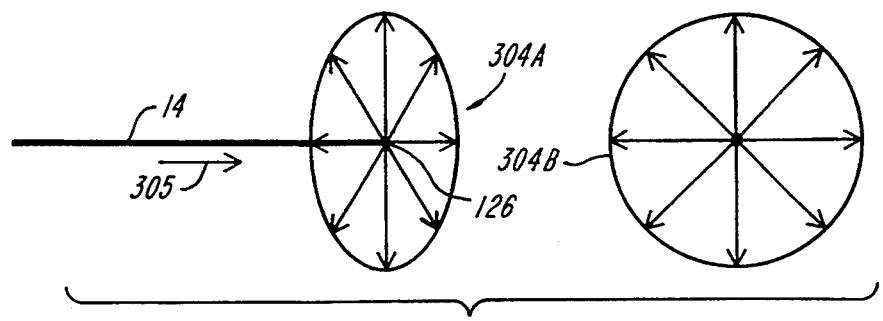
Figure 21D:
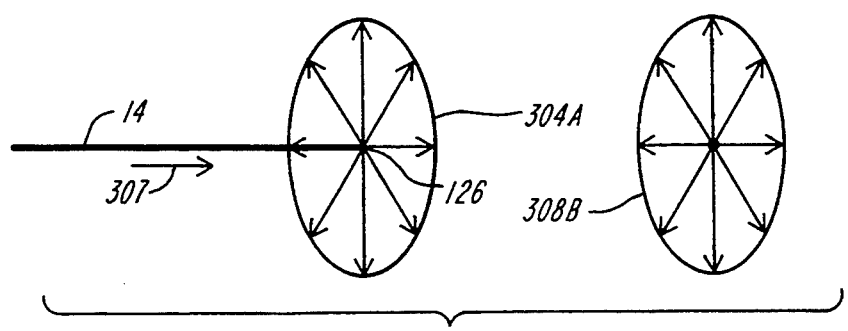
Figure 21E:
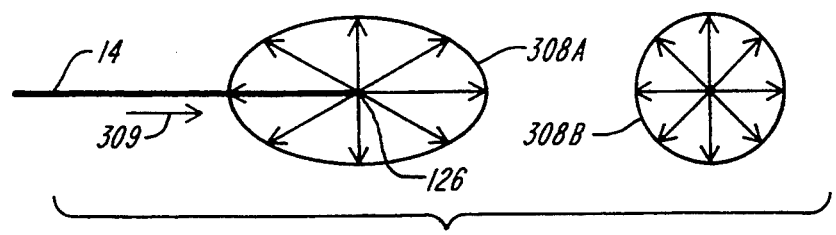
Figure 21F:
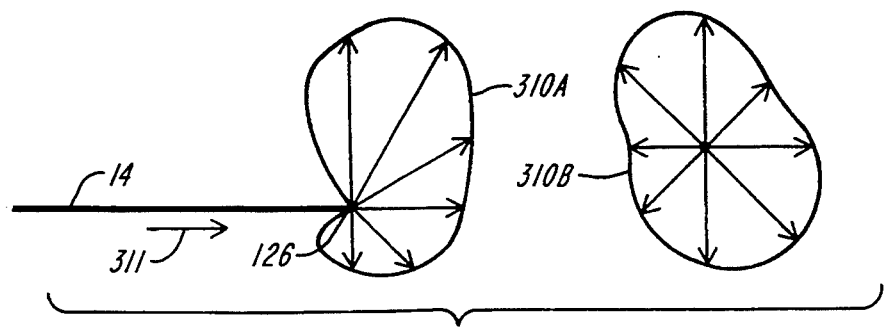

FIGS. 21A–21F depict examples of various isodose contours that can be achieved with the present invention. Specifically, FIG. 21A shows the probe 14 adapted to deliver isodose contours which form a sphere of radiation 300 centered about the probe tip 126. FIG. 21B shows the probe 14 adapted to deliver a sphere of radiation 302, wherein the probe tip 126 is offset from the center of the sphere 302. FIG. 21C shows the probe 14 having a tip 126 adapted to deliver a radiation field in the shape of an oblate ellipsoid (i.e., a "pancake" shape), as shown in perspective at 304A and looking along axis 305 at 304B. FIG. 21C depicts the probe 14 having a tip 126 adapted for delivering a radiation field in the shape of a prolate ellipsoid (i.e., a "cigar" shape), as shown in perspective at 306A and along axis 307 at 306B. As shown in FIG. 21D, the probe 14 enters the ellipsoid 306A along its minor axis. FIG. 21E shows the tip 126 also adapted for delivering a radiation field in the shape of a prolate ellipsoid. The ellipsoid is shown in perspective at 308A and along axis 309 at 308B. As can be seen, the probe 14 enters the ellipsoid 308A along its major axis. FIG. 21F depicts the probe tip 126 adapted for delivering an asymmetric radiation field shown in perspective at 310A and along axis 311 at 310B.

The design of a variable-thickness x-ray shield 128 for generating x-radiation principally within predetermined isodose contours will generally begin with digital data describing the size and shape of the desired irradiation volume (such as a tumor) which has been obtained by some method of imaging such as CT scan or Magnetic Resonance Imaging. From such data, and a knowledge of the x-ray absorption properties of the probe materials and of the shielding material used, the details of the thickness profile of the shield can be calculated. In general the isodose contours can assume many shapes and sizes and need not be symmetrical.

Various methods can be used to translate the design data into a physical shield. One method would be to use laser milling techniques. For instance, a hemispherical shield carrier 128A is coated with a layer of a metal with a high atomic number (e.g., Au) about 100 $\mu$m thick, the thickness of the shielding material deposited on the shield carrier 128A being well controlled in order to know how much material to remove in a subsequent milling process. One method of achieving a high degree of thickness control is to deposit the x-ray absorptive material by electroplating.

Figure 14:
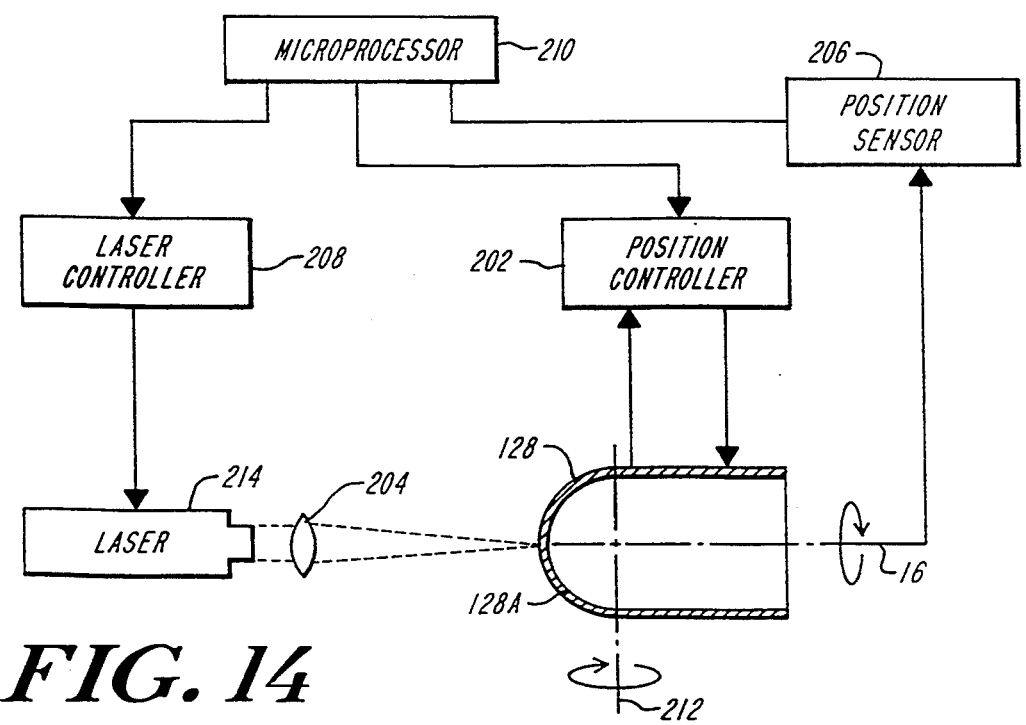
FIG. 14 is a block diagram of a laser milling system for generating variable thickness x-ray shields.

FIG. 14 shows a laser milling system 200 for generating an appropriate variable thickness x-ray shield 128 for delivery of predetermined x-ray isodose contours. It is well known that intense laser pulses can remove surface layers of metal. The laser milling system 200 of FIG. 14 comprises a mechanical positioning apparatus, shown generally as position controller 202, which systematically presents all of the surface points of the shield carrier 128A to a laser beam 204. For instance, the x-ray shield 128 and shield carrier 128A can be rotated about the probe axis 16 or an axis 212 which is normal to the probe axis 16. In a preferred embodiment, a microprocessor 210 has direct control over the motions of the position controller 202, and information as to the current position of the surface of the x-ray shield 128 is transmitted back to the microprocessor 210 to verify the specified position.

The specifications of the x-ray shield, i.e. the thickness profile, is calculated prior to the milling process, and from this data, the microprocessor 210 issues commands to a laser controller 208, which drives a laser 214, as to how much power is required to remove the correct amount of the shielding material at a particular irradiated surface point on the x-ray shield 128.

If the shielding material is entirely metallic, a powerful and expensive laser may be required in order to complete the milling process in an acceptable length of time. The preferred laser for these conditions is an excimer laser. However, when the shielding material consists of metal particles suspended in an organic material such as polyimide, then a much lower power laser, such as a nitrogen laser, may be used.

In another embodiment, the variable thickness x-ray shield 128 can be generated by controlled vapor deposition of the shielding material. This technique is also amenable to automation, and the pattern of deposition can be controlled by a microprocessor driven system.

In another embodiment, the shield material is first plated onto the carrier to the required maximum thickness of about 100 $\mu$m for gold, and then machined with a high accuracy CNC machine tool. This embodiment has the advantage of using a simple mechanical process and eliminates the need for an on-line gauging system as required for laser milling.

FIGS. 15A and 15B show one embodiment of a probe design which allows accurate angular alignment of the shield carrier 128A and thus, the x-ray shield 128 with the probe 14. A mechanical key, shown in the form of a tab 140 in the probe 14 and a corresponding groove 142 in the target assembly 126, can be provided between the two, to ensure accurate positioning of the x-ray shield 128 and the probe 14 in order to orient the x-ray emission pattern with the geometry of the desired irradiation volume. As one skilled in the art will appreciate, the keying arrangement of FIGS. 15A and 15B can also be used in combination with the target assembly 26 of FIG. 1.

As a further feature of the invention, steering may be used to direct the emitted electron beam to selected surfaces on the emission element, for example, where the target has different emission characteristics in different spatial regions. Control of the electron beam may be achieved under the control of telemetry, or by pre-programming the power source prior to implantation of all or part of the apparatus 10.

Figure 8:
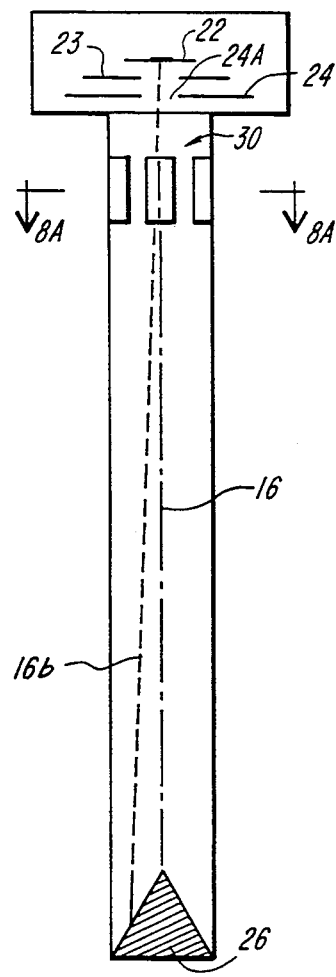
FIG. 8 is a perspective view of a beam steering assembly embodying the present invention.
Figure 8A:
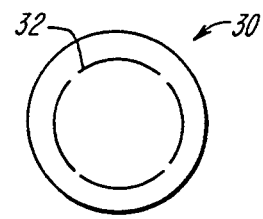

FIG. 8 shows an exemplary electrostatic beam steering assembly. In the illustrated embodiment, the cathode 22 generates electrons in a manner consistent with the above-described embodiments. The electrons are accelerated through a focusing electrode 23 toward the anode 24, and pass through an aperture 24A toward the target assembly 26. Enroute to target assembly 26, the electrons pass through an electrostatic deflection assembly 30, shown in cross-section at FIG. 8A. The assembly includes four deflectors 32. By varying the voltages applied to the opposing pairs of the deflectors 32, the electrons of the beam entering the assembly along axis 16A are deflected, or "steered" as they travel toward the target assembly 26 along axis 16B. Thus, the beam axis may be controlled to be straight or curved, as desired. As described below, electromagnetic techniques may alternatively be used to establish beam steering. In the latter case, the electrostatic deflective plates 32 may be replaced with magnetic deflector coils which are driven by currents to establish magnetic fields necessary to achieve a featured beam deflection.

In another form of the beam-steering embodiment, rather than pass through an electrostatic deflection assembly 30, the electron beam passes through a set of magnetic field-generating coils. The coils can be arranged in a configuration similar to the electrostatic deflection plates of the assembly 30. By varying the current through the coils, the resultant magnetic field is produced in a predetermined manner so as to influence the path of the electron beam.

In such a fashion, the electron beam may be steered to hit certain physical locations on a cone-shaped target assembly (FIG. 8), or a target of any other specific geometric configuration. By way of example, in the illustrated embodiment, a beam hitting the angled side of target assembly 26 will result in x-rays emitted off to that side, with little or no incidental radiation transmitted through to the opposite side of the target assembly.

In another form of the beam-steering embodiment, the x-ray emission characteristics may be controlled by spatially varying the emission parameters (such as radiation peak vs. energy) of the target assembly. By changing the emission peak (as a function of energy) at various points in the target assembly 26, for example, with a "bullseye" spatial pattern, the beam may be steered to regions of relatively high energy x-ray emission, or to regions of relatively low energy x-ray emission. Thus, the beam may be selectively directed to regions of the target assembly to achieve the required x-ray emission characteristic and direction.

As one skilled in the art will appreciate, the beam steering assembly of FIG. 8, can also be used in combination with the target assembly 126 of FIG. 12.

Figure 17:
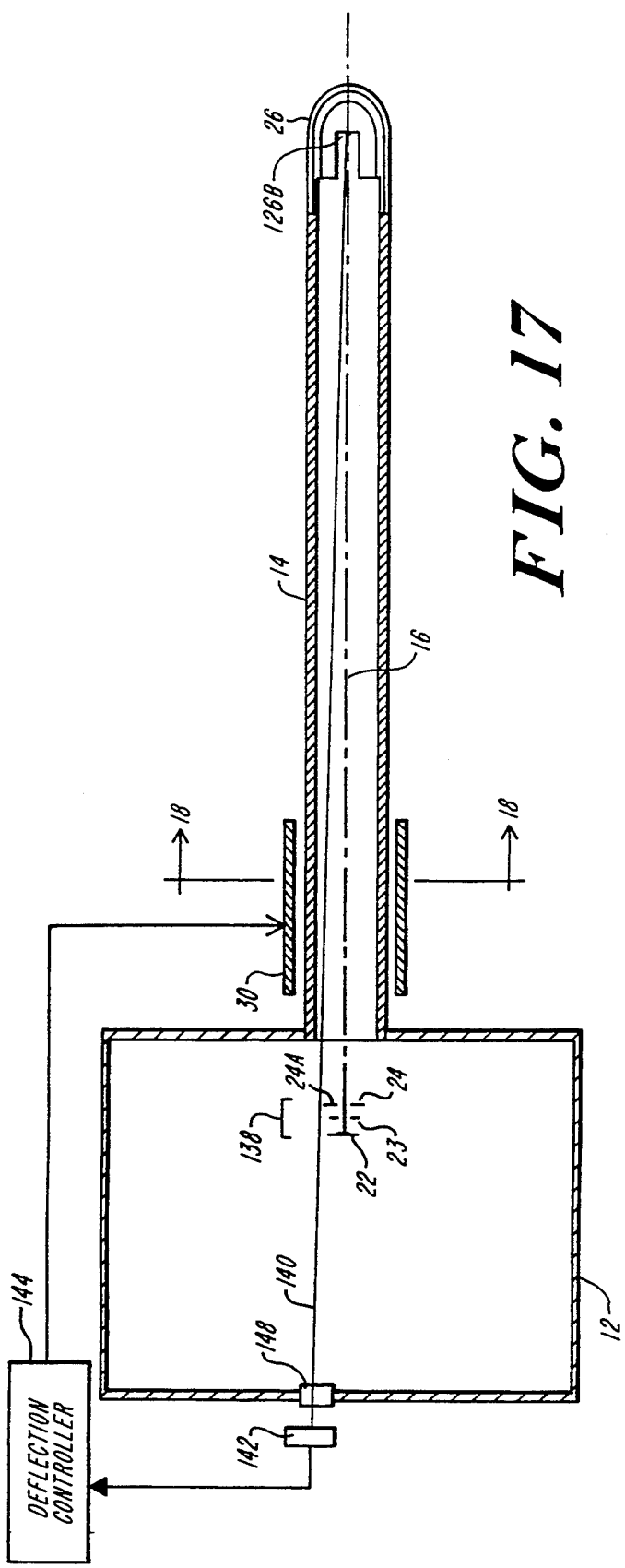
FIG. 17 is a cross-sectional view of a low power x-ray source having an external beam steering assembly which includes a feedback loop for electron beam positioning.
Figure 18:
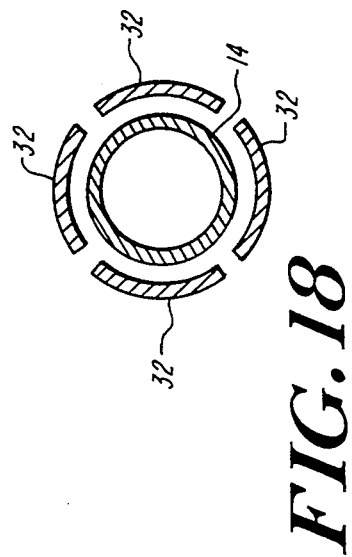
FIG. 18 is a cross-section view of the assembly of FIG. 17, taken along lines 16C.

FIGS. 16, 17 and 18 show an alternate beam steering assembly which includes a feedback loop system to accurately position the electron beam on the x-ray target 126B. In the illustrative embodiment, the deflection assembly 30 is substantially similar to that shown in FIG. 8, (except that it is a magnetic deflection system located outside of the probe) and an x-ray detector 142 is arranged to monitor x-rays emitted from the x-ray target 126B. The x-ray detector 142 can be positioned off axis with the electron beam, as shown, or placed on axis behind the cathode 22.

Changes in the trajectory of the electron beam can be measured when there are concomitant changes in the x-ray emission from the target 126B. A deflection controller 144, which is preferably driven by a microprocessor, can utilize the data from the x-ray detector 142 and, by controlling the voltages applied to the deflectors 32 of the deflection assembly 30, can appropriately position the electron beam.

For instance, the feedback loop system can be used to center the electron beam on a small x-ray target 126B. However, while a change in the monitor signal does indicate that the center of the beam has moved from the center of the target, there is no immediate information as to which direction the movement has taken place. Hence it may be necessary to periodically deflect the beam in a known direction and observe the behavior of the monitor signal in order to recenter the beam.

The monitor signal required to keep the beam positioned on the x-ray target 126B can be obtained by placing an x-ray detector 142 behind the electron optics 138 to monitor x-rays which are emitted back along the axis 16 of the probe 14. In FIGS. 16 and 17, the monitored x-rays 140 are shown to pass to one side of the electron optics 138. However, if the cathode is thin enough to be transparent to x-rays, it is possible to design the system such that the x-rays 140 pass through the electron optics 138 and the cathode 22. The detector 142 can be placed either within or outside of the housing 12 as shown in FIGS. 16 and 17, respectively. As illustrated in FIG. 17, if the detector 142 is located outside of the housing 12, an x-ray transmissive window 148 should be located in the wall of the housing to provide optical coupling of the detector 142 and x-ray target 126B.

After the beam has been accurately centered on the x-ray target 126B, the feedback system of FIGS. 16 and 17 can be used to optimize the electron-beam focus for maximum output of x-rays. For instance, this can be accomplished by maximizing the signal monitored by the feedback system by using the deflection controller 144 to adjust the voltages on the focus elements (such as focusing electrode 23) of the electron optics 138.

The feedback system illustrated in FIGS. 16 and 17 can also be used with the target assembly 26 shown in FIGS. 1 or 8. By way of example, the feedback systems can be used to position the electron beam so as to be incident upon a particular point of an emission element having regions of different emission characteristics (such as the bullseye spatial pattern described above). Additionally, the feedback system can be employed to control the acceleration voltage of the electron optics.

Figure 6:
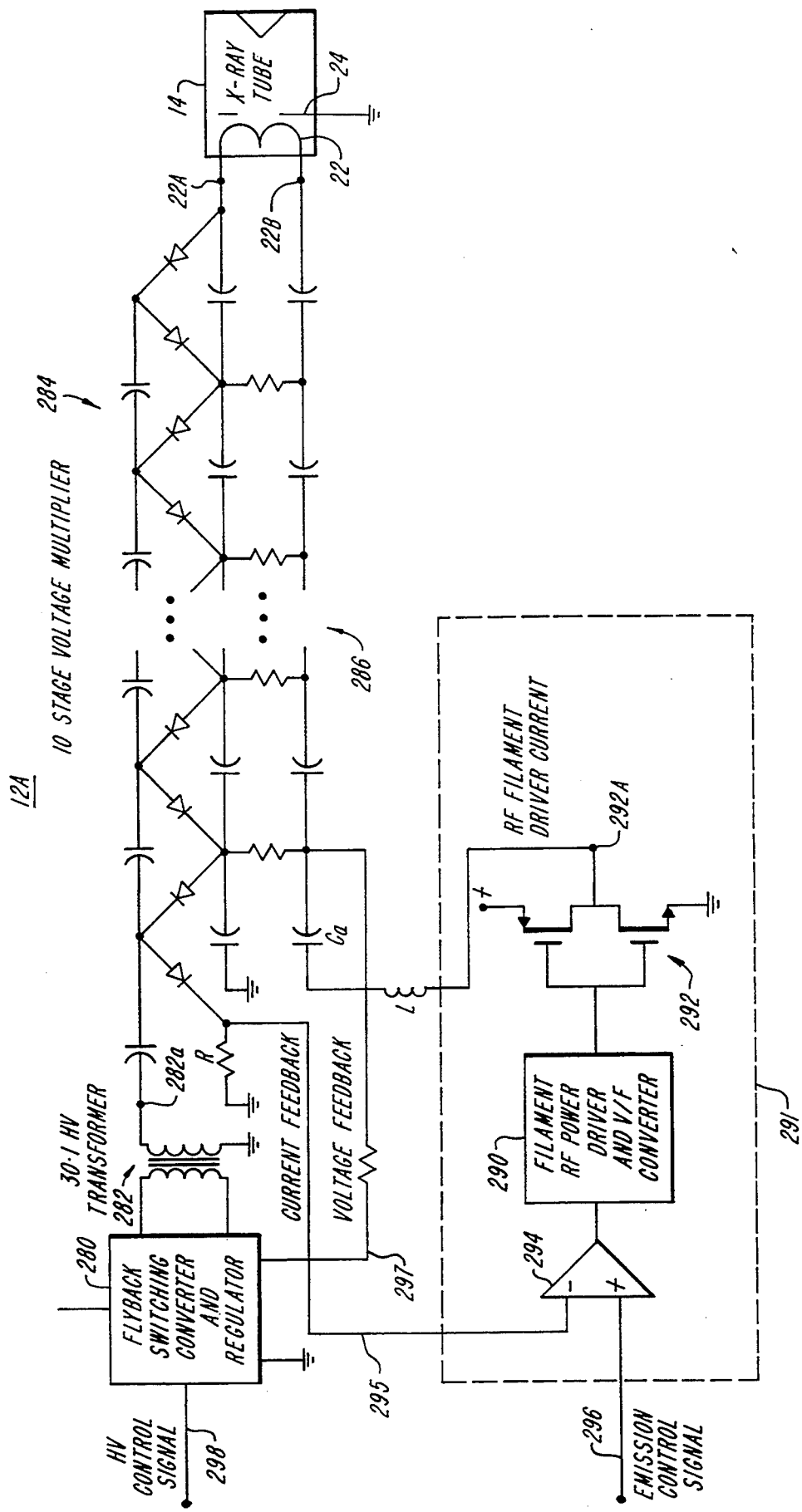
FIG. 6 is a detailed block diagram of a representative power supply of the embodiment of FIG. 1.
Figure 7:
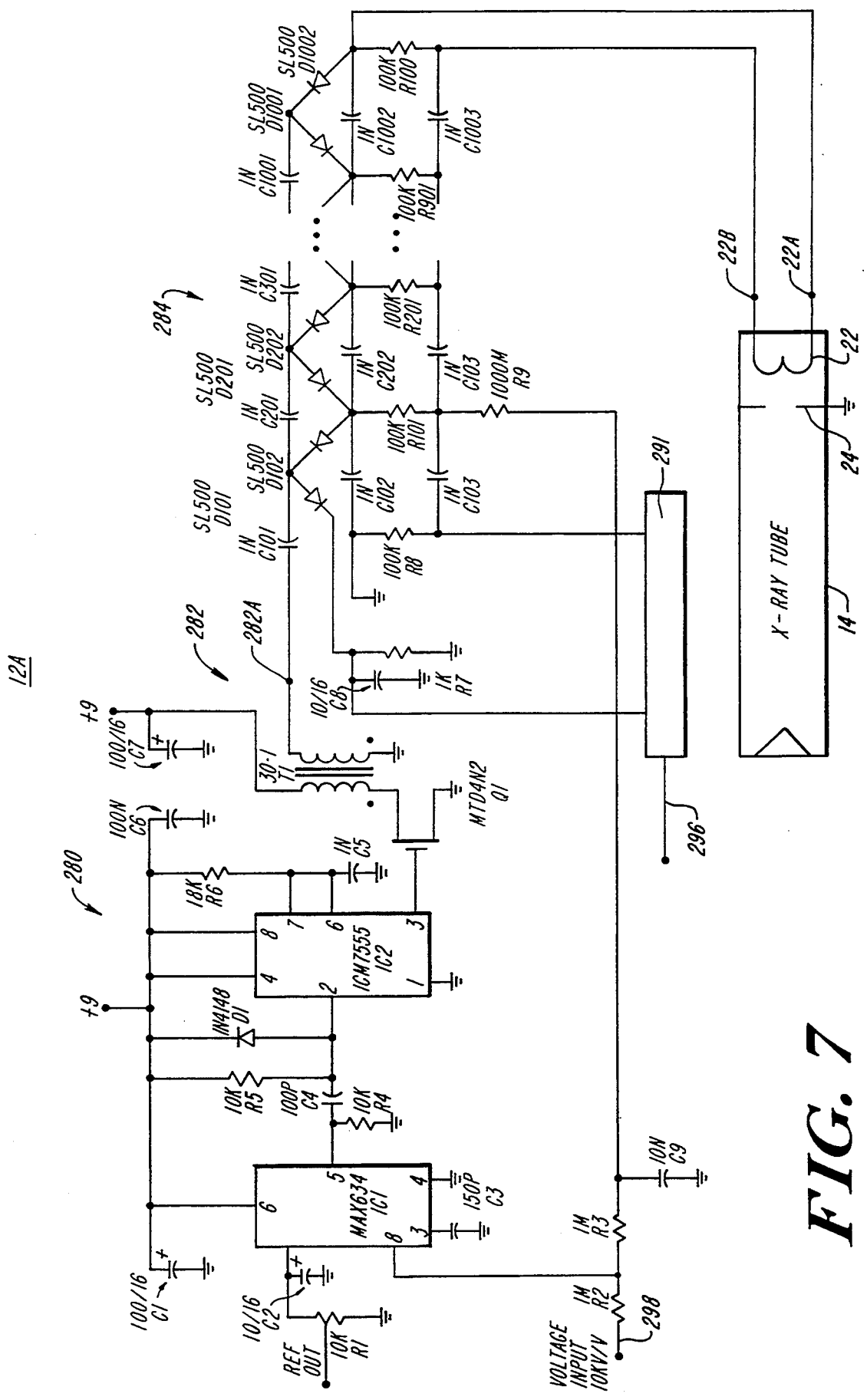
FIG. 7 is a detailed schematic diagram of power supply of FIG. 6.

As shown in the above-described embodiments, the apparatus 10 of FIG. 1 includes a power supply 12A. FIG. 6 is a block diagram of a representative supply 12A. FIG. 7 shows a more detailed schematic of the supply of FIG. 7. As shown in FIGS. 6 and 7, that embodiment includes a flyback switching converter and regulator 280, a 30:1 voltage transformer 282 coupled to a control voltage (or high voltage multiplier input) terminal 282A and a 10 stage voltage multiplier 284 coupled to a high voltage terminal 22A, and adapted to drive the filament of a thermionic emitter 22. A filament radio frequency power driver and voltage-to-frequency (V/F) converter 290 and an associated radio frequency filament driver 292 are coupled through current control terminal 292a and capacitor $C_o$ by way of a filament drive circuit 286 to the filament of emitter 22.

A difference amplifier 294 establishes a current feedback loop by driving the radio frequency power driver and V/F converter 290 in response to the detected difference between a current feedback signal on line 295 and an applied emission control signal on line 296. The latter signal may be selectively controlled to establish a desired temporal variation in the x-ray tube cathode current in filament of emitter (thermionic cathode) 22.

A high voltage amplitude feedback loop is established by the switching converter and regulator 280 in response to the detected difference between a voltage feedback signal on line 297 and an applied high voltage control signal on line 298. The latter signal may be selectively controlled to establish a desired amplitude variation of the potential at the filament of emitter (thermionic cathode) 22.

A more detailed description of the power supply shown in FIGS. 6 and 7 is provided in U.S. Pat. No. 5,153,900 and also in parent application U.S. Ser. No. 955,494.

FIG. 9 shows an exemplary system 300 adapted for x-ray treatment of brain tumors. System 300 includes a stereotactic frame 302 in combination with a low-power x-ray device 10A coupled thereto. In that configuration, x-ray device 10A is generally similar to the x-ray device 10 shown in FIG. 1, but has a cylindrical geometry. Corresponding elements of the two x-ray devices 10 and 10A are identified with the same reference designations. In general, stereotactic frames provide a fixed reference structure relative to the cranium of a patient. While the preferred embodiment described above is particularly adapted for use with this stereotactic frame, other embodiments of the invention might be similarly adapted for use with this or other frames or with general reference frames, for example, one establishing an operating fixture fixedly referenced to a part of the body other than the head. In the illustrated embodiment of FIG. 9, the stereotactic frame 302 is substantially similar to the Cosman-Roberts-Wells system manufactured by Radionics Inc., Burlington, Mass.

In the illustrated embodiment, the frame 302 establishes a reference XYZ coordinate system disposed about a desired origin point O. The frame 302 includes a generally U-shaped support element 304 defining a reference plane. Four arms 306A, 306B 306C and 306D (not shown) extend out from support frame 304. Each arm has a positioning pin 308. The pins 308 extend generally towards each other from the respective distal tips of arms 306A, 306B, 306C and 306D. In use, the four pins 308 are positioned against a patient's skull to establish a fixed positional relationship between the frame 302 and the patient's cranium. Thus, the frame 302 defines the reference XYZ coordinate system with respect to the patient's cranium.

An x-ray device support member 310 is coupled to the support element 304 by way of a pair of rotational coupling assemblies 312 and a pair of linear coupling assemblies 314. The x-ray device support member 310 includes an arcuate support track 310A. An x-ray device 10 is coupled to support track 310A by a coupling assembly 316. Coupling assembly 316 provides controlled movement of the x-ray device 10 on a circular path along track 310A and between an inner limit point and an outer limit point along axes (exemplified by axis 316') extending radially inward from the circular path of arcuate track 310A toward the origin point O.

In addition, rotation about the hubs of rotational coupling assemblies 312 allows the x-ray device support member 310 to be rotatably moved about the X axis. The x-ray device support member 310 is translocatable in a direction normal to the plane defined by the X and Y axes (the X-Y plane) by movement along tracks 314A, of the linear coupling assemblies 314. In the illustrative embodiment, a T-groove in tracks 314A mates with a tenon of block 314B which is affixed to member 304, permitting linear motion in the direction perpendicular to the X-Y plane. Set screws 332 in block 314B may be adjusted to lock the x-ray device support member 310 at a set height relative to the support frame 304.

X-ray support member 310 may be moved in the direction of the Z axis by movement of the tenons extending from member 310 in tracks 304A of support element 304. A controlled position of the member 310 along the tracks 304A can be established using locking screws 334.

In addition, support element 304 can be adjustably positioned in the direction of the X axis by sliding member 304 relative to its support member 305, and may be adjustably positioned with three degrees of freedom to establish a desired location of origin point O within the skull of a patient.

Figure 10:
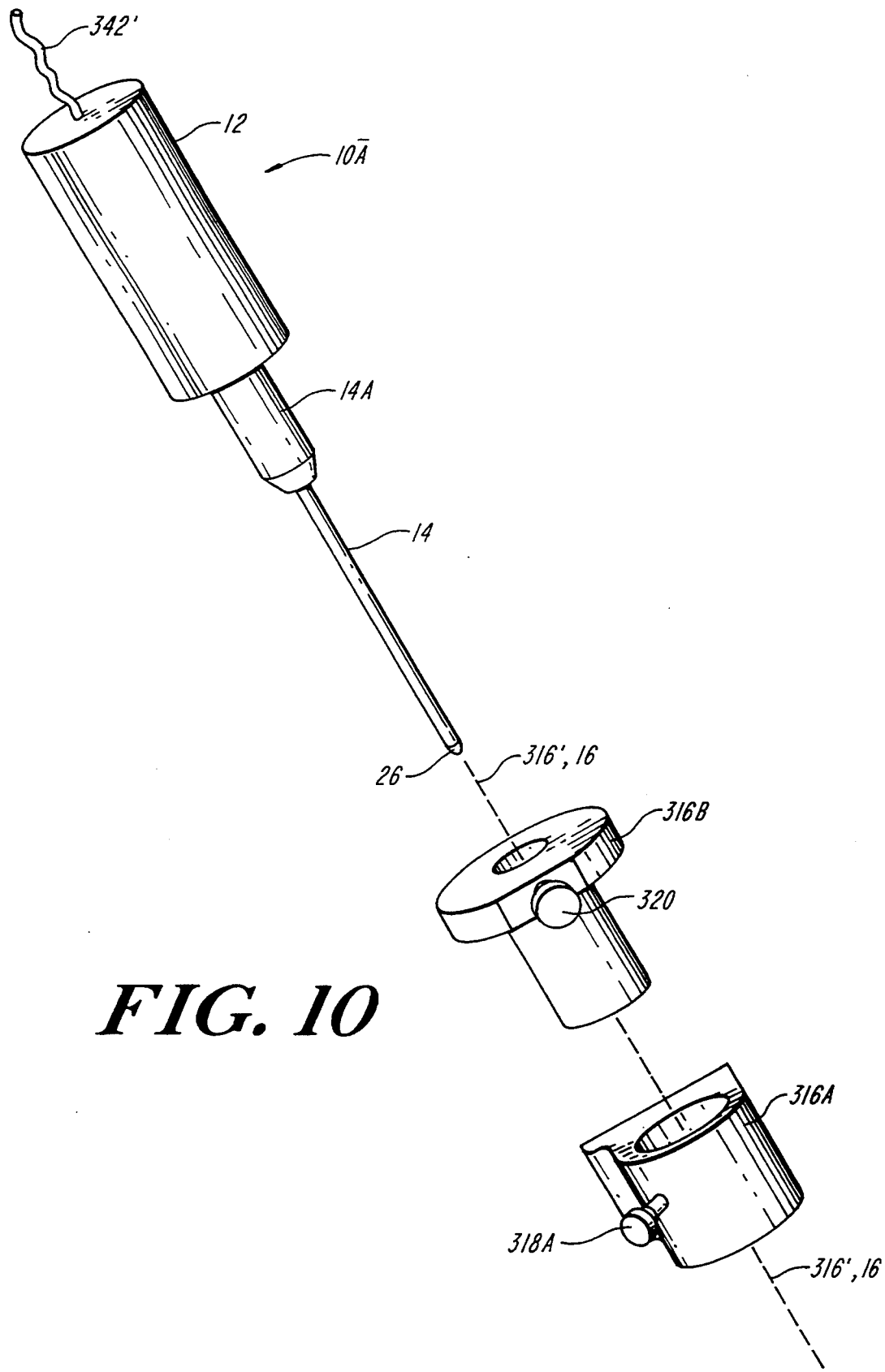
FIG. 10 is an exploded perspective view of an x-ray source and the coupling assembly of the system of FIG. 9.

The coupling assembly 316 is shown together with an x-ray device 10A, in exploded form, in FIG. 10. As shown, the coupling assembly 316 includes a receiver block 316A, a bushing element 316B, together with complementary shaped portions of the x-ray device 10A. As shown, the central axis 16 of probe 14 of x-ray device 10A is coaxial with axis 316'. The electron beam of probe 14 is nominally coaxially with axis 316', but may be adjustably varied as described above in conjunction with FIGS. 8, 8A, 16, 17, and 18 and below in conjunction with FIG. 10.

The cylindrical bushing element 316B is positioned partially within and coaxially with the receiver block 316A. The bushing element 316B is slidable (in the direction of radial axis 316') and may be selectively locked in place relative to block 316A using a set screw 318A. The bushing element 316B includes a central bore (with diameter D) extending along its central axis.

As noted above, the x-ray device 10A is similar to the x-ray device 10 shown in FIG. 1, but has a generally cylindrically shaped housing 12; the probe 14 includes a cylindrical shoulder portion 14A (having a diameter slightly less than D) immediately adjacent to housing 12, with a main portion with a small diameter (3.0 mm in the preferred embodiment). With this configuration, the x-ray device 10A may be positioned with its axis 16 coaxial with axis 316' and the shoulder portion 14A slidingly positioned within the bore of bushing element 316B. The relative position of x-ray device 10A may be fixed along axis 316' using set screws 320 of element 316B.

X-ray device 10A may include a magnetic deflection subsystem for its electron beam. The deflection subsystem includes magnetic deflection coils 32 as shown in FIG. 18 positioned about axis 16 within shoulder portion 14A. These coils are driven to adjustably control the position of the beam axis so that the beam is incident on the target of assembly 126 (shown, for example in FIGS. 16 and 17) in a desired manner. In the preferred form, radiation generated by device 10A is monitored (for example, by x-ray detector 142 shown in FIGS. 16 and 17, and/or an x-ray detector positioned outside the patient) and the deflector coils are driven accordingly by steering control currents on deflection X1, X2, Y1 and Y2 lines applied to the deflection coils, shown in FIG. 11.

As shown in FIG. 9, the microprocessor-based controller may not be disposed within the housing 12, but located external to the housing 12 in a control unit 342. Control unit 342 is coupled to x-ray device 10A by way of cable 342'. The elongated probe 14 of x-ray device 10 is configured so as to allow the probe 14 to pass through the track left by a biopsy needle, thereby permitting easy insertion of the probe 14 into the brain of a patient. For tumors composed of hard tissue, and where a biopsy needle smaller in width than the probe 14 is used, proper penetration into the tumor may require first widening the track left by the biopsy needle with intermediate sized needles.

With this configuration, the tip of probe 14 contains the x-ray emitting target and can be moved in and out relative to the cranial insertion site by movement along the axis 316'. The x-ray device 10A can be secured at a given position along by set screws 318A and 320. The length of probe 14 of x-ray device 10A is chosen such that the center of curvature of the tip of probe 14, when fully inserted down to the lower limit position along the axis 316' of 316A, is positioned exactly at the origin point O; when the x-ray apparatus 10 is fully withdrawn to the upper limit point along axis 316', the distal tip of the probe 14 is intended to be outside the patient's skull. The coordinates of the arcuate support track 310A can be set such that the origin point O is located at the desired isocenter of irradiation. Thus, by the rotation of x-ray device 10A support member 310 and the positioning of the x-ray device 10A along the circumferential track of the arcuate support track 310A and along axis 316', a user can choose the appropriate path (preferably of least destruction) for insertion of probe 14 into a patient's brain, the tip of probe 14 always positioned the origin point O upon full insertion of the probe 14 to the lower limit point.

Figure 11:
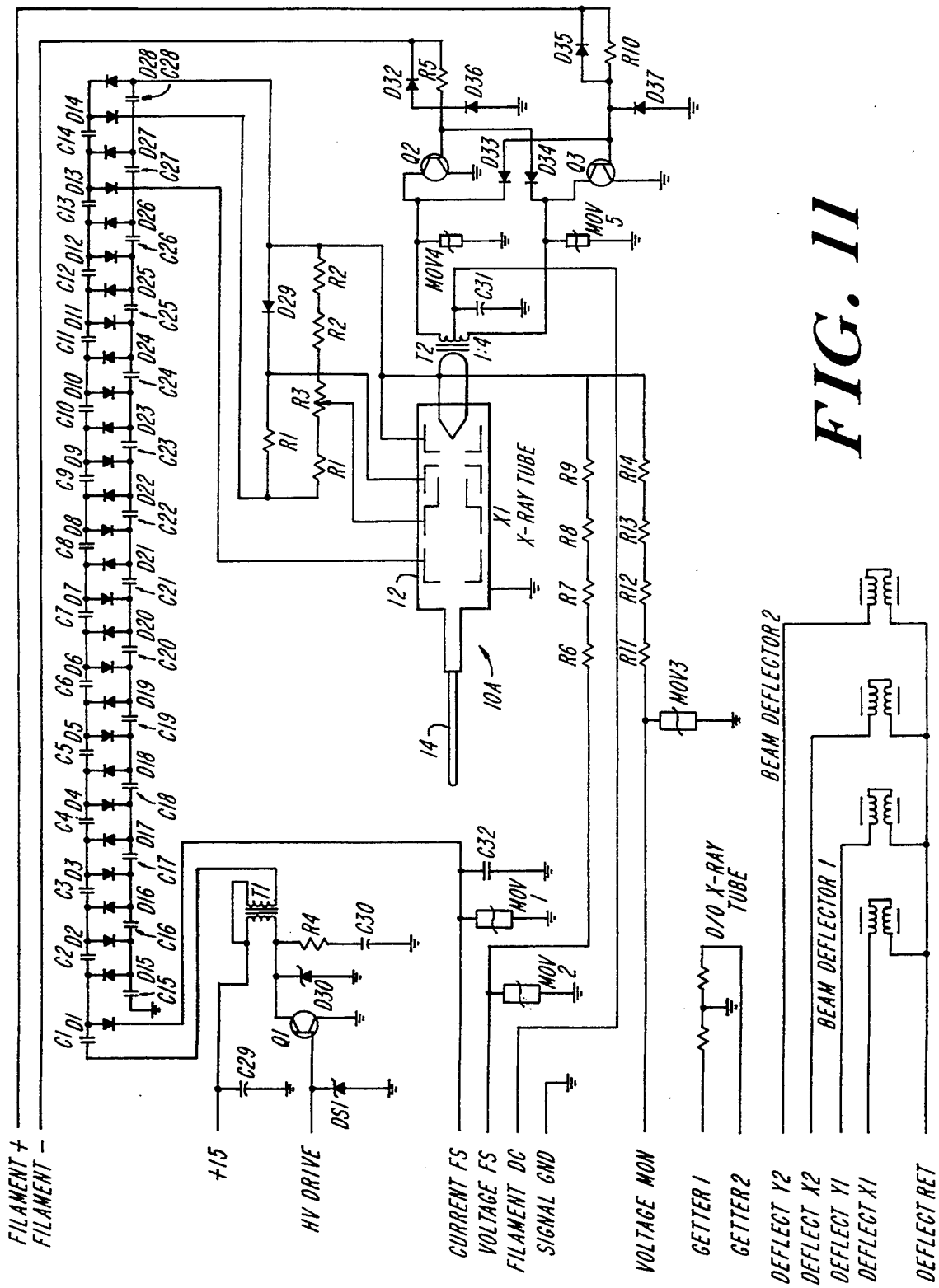
FIG. 11 is a schematic diagram of a representative high voltage power supply of the x-ray source of FIG. 10.

FIG. 11 shows a schematic diagram of a preferred high voltage power supply 12A for use with the x-ray device 10A of FIGS. 9 and 10. In that power supply, the HV drive signal is a 0 to 9 Volt drive signal. This signal drives the Flyback Switching Field Effect Transistor (FET) Q1, which in turn drives the HV Flyback transformer. The HV Flyback transformer steps up the +12 Volts to several thousand volts. The HV multiplier, D1 to D28, in turn steps up the voltage to the desired output voltage of 15 to 40 kV. The voltage feedback line provides feedback information to controller 12C, so that the output voltage of the HV multiplier can be held at a constant value.

The Filament + and − lines provide complementary 9 Volt 250 kHz square wave drive signals to FET's Q2 and Q3. These FET's chop the variable Filament DC voltage into an AC voltage, and drive the Filament/HV Isolation Transformer T2. Using a high frequency signal to drive this transformer permits a single turn secondary to drive the x-ray tube filament. This in turn permits miniaturizing the transformer while maintaining the necessary high voltage isolation. The current FB line allows controller 12C to sense the beam current, and the controller then adjusts the Filament DC Voltage for the desired beam current, by providing the appropriate heating current to the thermionic emitter 22. The Deflection X1, X2, Y1, Y2 lines provide current drive signals to the magnetic beam deflection coils.

As discussed above with respect to FIG. 1, the apparatus 10 includes beam generation and acceleration components to generate and accelerate electrons, prior to those electrons entering the probe 14. The generated electron beam then flows through probe 14, impacts the target 26b, and thereby produces x-rays. In the absence of magnetic fields, the electrons flowing through the probe 14 follow a straight-line trajectory. Consequently, the probe 14 is typically rigid without any bends.

However, in certain medical applications it is beneficial to use a flexible probe. One such application involves threading the x-ray source down an existing pathway, such as the trachea. Another such application involves maneuvering the x-ray source around critical structures, such as a nerves or blood vessels.

Figure 20A:
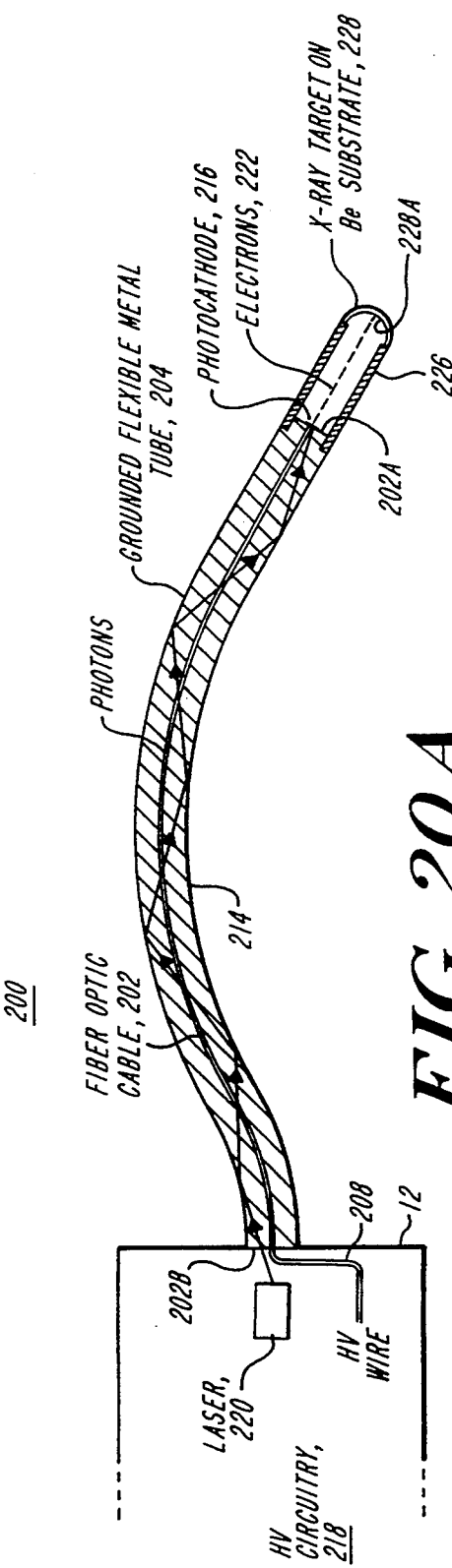
FIGS. 20A and B are cross-sectional views of a flexible probe which incorporates a photoemitter located within the target assembly.

FIG. 20A shows a diagram of apparatus 200 including a flexible probe 214. The apparatus 200 includes a high voltage network 218, a laser source 220, a probe assembly 214, and a target assembly 226. According to one aspect of the invention, the apparatus 200 provides the required flexibility, without using strong magnetic fields, by locating electron generating and accelerating components in the target assembly 226. The probe assembly 214 couples both the laser source 220 and the high voltage network 218 to the target assembly 226. The probe assembly includes flexible fiber optical cable 202 enclosed in a small-diameter flexible metallic tube 204.

The target assembly 226, which can be for example 1- to 2- cm in length, extends from the end of the probe assembly 214 and includes a shell which encloses the target 228. According to one embodiment, the target assembly 226 is rigid in nature and generally cylindrical in shape. In this embodiment the cylindrical shell enclosing the target assembly can be considered to provide a housing for the electron beam source as well as a tubular probe extending from the housing along the electron beam path. The inner surface 226A of the assembly 226 is lined with an electrical insulator, while the external surface 226b of the assembly 226 is electrically conductive. According to a preferred embodiment, the target assembly is hermetically sealed to the end of the probe assembly 214, and evacuated. According to another embodiment, the entire probe assembly 214 is evacuated.

The terminal end 202A of the fiber optical cable 202 is preferably coated, over at least part of its area, with a semitransparent photoemissive substance such as, Ag-O-Cs, thus forming a photocathode 216. A high voltage conductor 208, embedded in the fiber optical cable 202, conducts electrons to the cathode 216 from the high voltage network 218. Similarly, the flexible tube 204 couples a ground return from the target 228 to the high voltage network 218, thereby establishing a high voltage field between the cathode 216 and the target 228. The fiber optical cable 202 acts as an insulating dielectric between the high voltage conductor 208 and the grounded flexible tube 204.

Figure 20B:
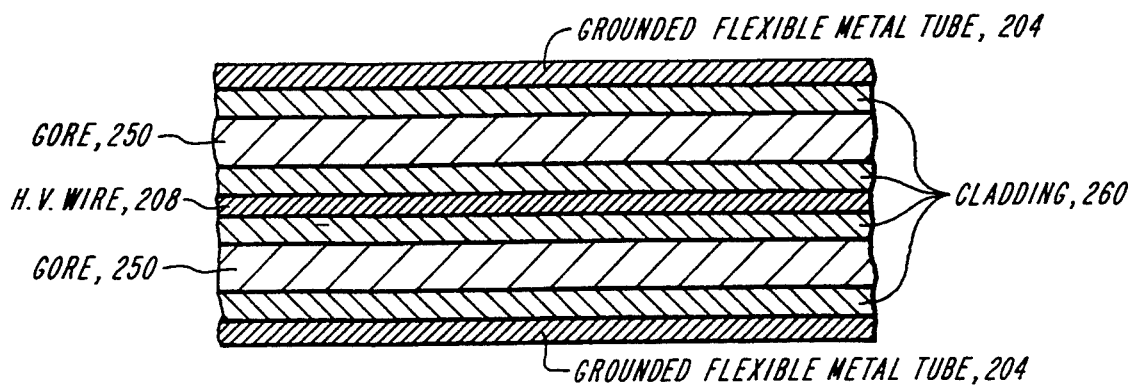

In one embodiment, to eliminate absorption and scattering of the light out of the fiber optic cable 202 by the high voltage wire 208, the fiber optic cable 202 can have an annular configuration, as shown in cross-section in FIG. 20B. The light from the laser 220 travels down the annular core 250 of the fiber optic cable 202. Cladding 260 on each side of the core 250 has an index of refraction so as to refract the light beam incident on the interface back into the core 250. A grounded flexible metal tube 204 surrounds the outer cladding 260.

As in previously described embodiments, the target 228 can be for example, beryllium, (Be), coated on one side with a thin film or layer 228A of a high atomic number element, such as tungsten (W) or gold (Au).

In operation, the small semiconductor laser 220 shining down the fiber optical cable 202 activates the transmissive photocathode 216 which generates free electrons 222. The high voltage field between the cathode 216 and target 228 accelerates these electrons, thereby forcing them to strike the surface 228A of target 228 and produce x-rays. In order to generate, for example, 20 $\mu$A of current from an Ag-O-Cs photocathode 216 with a laser 220 emitting light at a wavelength of 0.8 $\mu$m, the 0.4% quantum efficiency of this photocathode 216 for this wavelength requires that the laser 220 emits 7.5 mW optical power. Such diode lasers are readily commercially available. According to the invention, the photoemissive surface which forms cathode 216 can, in fact, be quite small. For example, for a current density at the cathode 216 of 1 A/cm$^2$, the photoemitter's diameter need only be approximately 50 $\mu$m.

Figure 22:
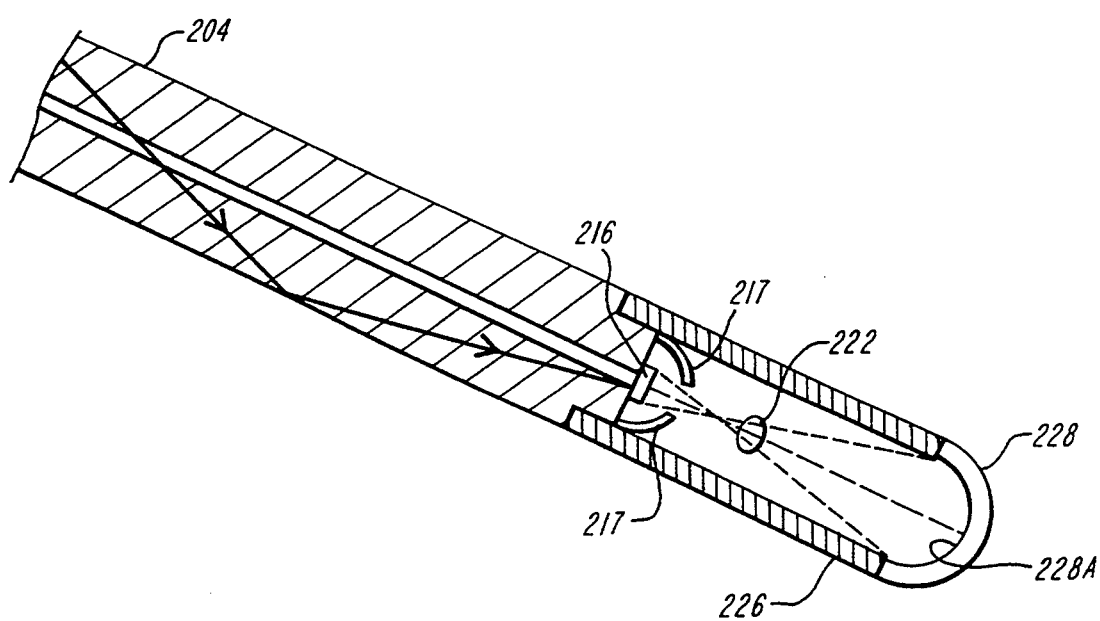
FIG. 22 shows a schematic representation, in section, of a probe tip having a shield positioned adjacent to the photocathode of the source of FIG. 20A.

Acceleration of the free electrons 222 in a high voltage field of 30 to 50 kV may cause positive ions to be impact generated in the then film 228A of the target 228. These ions will accelerate toward the photocathode 216 striking and possibly damaging its surface. As shown schematically in FIG. 22, in one embodiment to minimize ion bombardment of the photocathode 216, a high electrical impedance (toroidal shell) shield 217 is positioned in close proximity, and electrically coupled along its outer edge to the photocathode. A small hole 217A in this shield 217 focusses the free electrons 222 and disperses then over the target 228. The returning ions impinge on the shield 217 instead of the photocathode 216.

One difficult fabrication aspect of this invention is the fabrication of the photocathode 216, which for practical substances, with reasonable quantum efficiencies above 10$^{-3}$, should be performed in a vacuum. This procedure can be carried out with the fiber optical cable 202 positioned in a bell jar, where for example, an Ag-O-Cs photosurface is fabricated in the conventional manner. Subsequently, without exposure to air, the optical cable 202 can be inserted into the tube 204 and the photocathode 216 placed in contact with the shield 217. The end 202B can be vacuum sealed to the flexible tube 204. In the above embodiments, the probe 14 or 214, along with its associated target assembly 26, 126, or 226, can be coated with a biocompatible outer layer, such as titanium nitride on a sublayer of nickel. For additional biocompatible protection a sheath of, for example, polyurethane can be fitted over the probe, such as that illustrated in FIG. 2.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An x-ray source comprising,
    A. a housing enclosing a beam generation means for generating an electron beam along a beam path, said beam generation means including an electron source;
    B. an elongated tubular probe extending along a central axis from said housing and about said beam path;
    C. a target assembly including a target element, wherein said target element being responsive to electrons incident thereon to emit x-rays, said target assembly including means for coupling said assembly to the end of said probe distal from said housing whereby said target assembly is positioned along said beam path; and
    D. a beam steering assembly, wherein said beam steering assembly includes:
        i. deflection means for deflecting said beam from a nominally straight axis to an axis intersecting a selected surface region on said target element in response to a deflection control signal,
        ii. a feedback network including deflection sensing means for sensing said deflection of said beam and means for generating a feedback signal representative thereof, and
        iii. a deflection controller coupled to said deflection means and to said feedback network, and including means for generating said deflection control signal in response to said feedback signal.

2. An x-ray source according to claim 1 wherein said deflection sensing means includes x-ray sensing means for sensing x-ray emissions from said target element.

3. An x-ray source according to claim 2 wherein said x-ray sensing means is located proximate to said electron source.

4. An x-ray source according to claim 3 wherein at least a portion of said emitted x-rays propagate from said target assembly to said x-ray sensing means.

5. An x-ray source according to claim 3 wherein said electron beam source is positioned between said target element and said x-ray sensing means and at least a portion of said emitted x-rays propagate through said electron beam source to said x-ray sensing means.

6. An x-ray source according to claim 2 wherein said x-ray sensing means is located outside of said housing.

7. An x-ray source according to claim 2 wherein said feedback controller includes means for controlling said deflection for said beam, whereby said x-ray sensing means senses a maximum x-ray emission from said target element.

8. An x-ray source according to claim 1 wherein said beam steering assembly includes calibration means for periodically deflecting said beam along at least one predetermined directional axis to calibrate said deflection sensing means.

9. An x-ray source according to claim 1 wherein said beam steering assembly includes means for deflecting said beam along at least one predetermined directional axis, and wherein said target assembly includes carrier means for supporting said target element, and wherein one or more boundaries are formed between said carrier means and said target element such that each of said boundaries defines corresponding fiducial edges transverse to said directional axis.

10. An x-ray source according to claim 9 wherein two of said boundaries are formed and wherein said beam is deflected along two predetermined directional axes such that said predetermined directional axes are mutually perpendicular.

11. An x-ray source according to claim 10, wherein said deflection means includes positioning means for controlling said beam to be incident on the center of said target, and includes:
   i. means for sweeping said beam across said target in a first (x) direction orthogonal to said beam path and detecting fiducial edges in said sweep and in response thereto determining the x-direction reference point on said target between said detected fiducial edges,
   ii. means for sweeping said beam across said target in a second (y) direction, wherein said y direction is orthogonal to said x direction and said beam path and detecting fiducial edges in said sweep and in response thereto determining the y-direction reference point on said target between said detected fiducial edges,
   iii. means for generating said control signal to be representative of said x-direction mid-point and said y-direction reference point, and
   iv. means for applying said control signal to said deflection means whereby said beam is incident on a desired point on said target as viewed from said source.

12. An x-ray source according to claim 11 wherein said x-direction reference point is the mid-point along a line connecting said detected fiducial edges along said x-direction sweep, and said y-direction reference point is the mid-point along a line connecting said detected fiducial edges along said y-direction sweep.

13. An x-ray source according to claim 10 wherein said deflection means includes target acquisition means including:
   i. means for controlling said beam to sweep in a raster scan pattern at said end of said probe distal from said housing,
   ii. identifying a scan in which said beam traverses said target element and detecting fiducial edges along said scan and in response thereto determining a first reference point along said identified scan.

14. An x-ray source according to claim 13 wherein said first reference point is the mid-point between two fiducial edges detected along said identified scan.

15. An x-ray source according to claim 14 further comprising:
   i. means for generating said control signal to be representative of said first reference point,
   ii. means for applying said control signal to said deflecting means whereby said beam is positioned along a perpendicular bisector of a line connecting said fiducial edges of said identified scan,
   iii. means for sweeping said beam along a directional axis perpendicular to said line and detecting fiducial edges along said directional axis and in response thereto determining a second reference point along said directional axis between said detected fiducial edges, said second reference point being the mid-point along said directional axis between said detected fiducial edges,
   iv. means for generating said control signal to be representative of said first and second reference points, and
   v. means for applying said control signal to said deflection means whereby said beam is incident on the center of said target as viewed from said source.

16. An x-ray source according to claim 1 wherein said deflection controller is located in said housing.

17. An x-ray source according to claim 1 wherein said deflection controller is located outside of said housing.

18. An x-ray source according to claim 2 wherein said electron beam is characterized by a beam current and said electron beam source further includes controller means responsive to said x-ray sensing means for adjusting said beam current in response to sensed x-ray emissions from said target element.

* * * * *